(12) United States Patent
De Araujo et al.

(10) Patent No.: US 9,040,775 B2
(45) Date of Patent: May 26, 2015

(54) METHOD FOR MODIFYING PLANT ARCHITECTURE AND ENHANCING PLANT BIOMASS AND/OR SUCROSE YIELD

(75) Inventors: Paula Gonçalves De Araujo, San Paulo (BR); Jesus Aparecido Ferro, San Paulo (BR); Marcos Alegria, San Paulo (BR); Ricardo Augusto Dante, San Paulo (BR)

(73) Assignee: Monsanto Do Brasil LTDA., Sao Paulo (BR)

( * ) Notice: Subject to any disclaimer, the term of this patent is extended or adjusted under 35 U.S.C. 154(b) by 385 days.

(21) Appl. No.: 13/415,544

(22) Filed: Mar. 8, 2012

(65) Prior Publication Data

US 2012/0192313 A1 Jul. 26, 2012

Related U.S. Application Data

(63) Continuation of application No. 12/445,548, filed as application No. PCT/BR2007/000294 on Oct. 26, 2007, now Pat. No. 8,158,854.

(60) Provisional application No. 60/863,252, filed on Oct. 27, 2006.

(51) Int. Cl.
  *C12N 15/82* (2006.01)
  *C12N 9/02* (2006.01)

(52) U.S. Cl.
  CPC .......... *C12N 15/8261* (2013.01); *C12N 9/0071* (2013.01); *C12N 15/8245* (2013.01)

(58) Field of Classification Search
  None
  See application file for complete search history.

(56) References Cited

U.S. PATENT DOCUMENTS

| | | |
|---|---|---|
| 6,455,675 B1 | 9/2002 | Lange et al. |
| 7,834,146 B2 | 11/2010 | Kovalic et al. |
| 2004/0034888 A1* | 2/2004 | Liu et al. ........................ 800/289 |
| 2004/0172684 A1 | 9/2004 | Kovalic et al. |

FOREIGN PATENT DOCUMENTS

WO 94/28141 A1 12/1994

OTHER PUBLICATIONS

Biemelt et al. (2004) Plant Physiology 135:254-265.*
Mitchum et al. (2006) Plant Journal 45:804-818.*
Roemmelt et al., "Formation of novel flavonoids in apple (Malusxdomestica) treated with the 2-oxoglutarate-dependent dioxygenase inhibitor prohexadione-Ca", Phytochemistry, 2003, pp. 709-716, vol. 64, No. 3, Medline abstract NLM1367909 retrieved on Jan. 15, 2008.
Radi et al., "Ectopic Expression of Pumpkin Gibberellin Oxidases Alters Gibberellin Biosynthesis and Development of Transgenic *Arabidopsis* Plants", Plant Physiology, Feb. 2006, pp. 528-536, vol. 140, No. 2, American Society of Plant Biologists.
Curtis et al., "Induction of Dwarfism in Transgenic *Solanum Dulcamara* by Over-expression of a Gibberellin 20-oxidase cDNA from Pumpkin", Plant Journal, Aug. 2000, pp. 329-338, vol. 23, No. 3.
Hedden, "Recent Advances in Gibberellin Biosynthesis", Journal of Experimental Botany, May 1999, pp. 553-563, vol. 50, No. 334.
Guimaraes et al., "Sugarcane Growth, Sucrose Accumulation and Invertase Activities Under Trinexapac-ethyl Treatment", Cientifica (Jaboticabal), 2005, pp. 20-26, vol. 33, No. 1.
Database UniProt [Online] Mar. 1, 2003, Buell et al., "Putative gibberellin 20-oxidase", XP-002576758, retrieved from EBI Database accession No. Q8H0A8, 3 pages.
International Serch Report PCT/BR2007/000294 dated Jan. 15, 2008.
Supplemental European Search Report EP 07815735 dated May 12, 2010.
Mitchum et al., "Distinct and Overlapping Roles of Two Gibberellin 3-Oxidases in *Arabidopsis* Development", Plant Journal, 2006, pp. 804-818, vol. 45, Blackwell Publishing Ltd.
Biemelt et al., "Impact of Altered Gibberellin Metabolism on Biomass Accumulation, Lignin Biosynthesis, and Photosynthesis in Transgenic Tobacco Plants", Plant Physiology, May 2004, pp. 254-265, vol. 135, American Society of Plant Biologists.
Spielmeyer et al., "Semidwarf (sd-1), "Green Revolution" Rice, Contains a Defective Gibberellin 20-Oxidase Gene", Proceedings of the National Academy of Sciences, Jun. 25, 2002, pp. 9043-9048, vol. 99, No. 13.

* cited by examiner

*Primary Examiner* — Russell Kallis
*Assistant Examiner* — Steven Bernacki
(74) *Attorney, Agent, or Firm* — Thompson Coburn LLP; J. Wendy Davis

(57) ABSTRACT

The present invention relates to methodology and constructs for modifying plant architecture and enhancing plant biomass and/or sucrose yield.

4 Claims, 14 Drawing Sheets

Figure 1

C_SeqList_substitute.TXT" which is 24300 bytes
METHOD FOR MODIFYING PLANT ARCHITECTURE AND ENHANCING PLANT BIOMASS AND/OR SUCROSE YIELD

CROSS-REFERENCE TO RELATED APPLICATIONS

This application is a continuation of U.S. patent application Ser. No. 12/445,548, filed Apr. 14, 2009, now U.S. Pat. No. 8,158,854, which was the National Stage of International Application No. PCT/BR2007/000294 filed Oct. 26, 2007, which claims the benefit of U.S. Provisional Patent Application No. 60/863,252, filed Oct. 27, 2006, the disclosure of all of which are herein incorporated by reference in their entireties.

INCORPORATION OF SEQUENCE LISTING

A Sequence Listing is contained in the file named "49-75_56812_C_SeqList_substitute.TXT" which is 24300 bytes (measured in MS-Windows®) and was created on Oct. 16, 2013, and comprises 64 nucleotide sequences, and is herein incorporated by reference in its entirety.

FIELD OF THE INVENTION

The present invention relates to the field of molecular biology and the phenotypic alteration of plant characteristics through the introduction of foreign genes into plant cells, preferably into their genomes. More particularly, the present invention pertains to methods and compositions for producing transgenic plants having modified plant architecture and enhanced biomass and/or sucrose yield with respect to non-transgenic plants grown in similar conditions.

BACKGROUND

Sugarcane is one of the most photosynthetic efficient cultivated crops. Sugarcane average annual yields in Brazil, world's largest producer, range from 80 to 120 tons/ha. Yet, the productivity potential of 300 tons of biomass per hectare has been suggested. Alexander, THE ENERGY CANE ALTERNATIVE (Elsevier, 1985)

The utilization of biomass has been the subject of strong interest recently, particularly with respect to the efforts to develop methods to produce alternate fuels that use non-starch, non-food-related biomass, such as trees, grasses and waste materials, which would expand the available resource base for sugars and would lower cost sources. In Brazil, sugarcane mills have developed technologies for large-scale sucrose fermentation for producing fuel ethanol. In the 2006/2007 crop, approximately 18 billion liters of sugarcane-derived ethanol were produced. In addition to providing a renewable source of fuel, sugarcane-based fuel provides a means for reducing $CO_2$ emissions.

Over the centuries, sugarcane was cultivated almost solely as a source of sucrose, which accumulates at high concentrations in the stem internodes. The sucrose then is extracted and purified in large mill factories, and is used as a raw material in food industries.

While sugarcane is photosynthetically efficient, the average productivity of commercial sugarcane plantations around the world is limited by the highly polyploid nature of the sugarcane genome, which renders sugarcane not amenable to most of the breeding techniques developed for diploid species. Because traditional breeding programs have provided limited success in producing high-yielding plants, cultivated sugarcane varieties are clones derived from interspecific crosses between Saccharum officinarum with its relatives, most often S. spontaneum but also S. sinense or S. barberi, whose progenies were backcrossed to S. officinarum. On the other hand, the emergence of molecular genetics approaches to manipulating plant genomes has offered researchers a means for developing crops with improved properties or traits, through introduction and expression of recombinant nucleic acid molecules in plants.

SUMMARY OF THE INVENTION

In one aspect, the invention provides a transgenic plant belonging to a family selected from the group consisting of Poaceae, Cucurbitaceae, Cruciferaceae, Solanaceae, Leguminosae, and Apocynaceae plant family, wherein the plant contains an endogenous Ss2-ODD1 DNA sequence the expression of which is reduced compared to a wild-type control plant. In further embodiment, the plant belongs to Poacea family. In even further embodiments, the transgenic plant is sugarcane, sorghum, corn and Miscanthus. In another embodiment the expression, of Ss2-ODD1 DNA sequence is reduced by antisense suppression, sense co-suppression, RNA interference, or enzymatic RNA.

In another aspect, the invention provides a method for producing sucrose, comprising: (a) providing a transgenic plant having suppressed Ss2-ODD1 protein levels; and (b) obtaining sucrose from said plant. In one embodiment, the plant is sugarcane or sorghum.

In another aspect, the invention provides a method for producing biomass, comprising: (a) providing a transgenic plant having suppressed Ss2-ODD1 protein levels; and (b) obtaining biomass from said plant. In one embodiment, the plant is sugarcane or sorghum.

In another aspect, the invention provides a method for enhancing sucrose yield in a plant, comprising: suppressing Ss2-ODD1 protein levels in said plant. In one embodiment, the plant is sugarcane or sorghum.

In another aspect, the invention provides a method for enhancing biomass in a plant yield, comprising: suppressing Ss2-ODD1 protein levels in said plant. In one embodiment, the plant is sugarcane or sorghum.

In another aspect, the invention provides a nucleic acid construct comprising an Ss2-ODD1 sequence. In further embodiment, the invention provides a transgenic plant or cell comprising the nucleic acid construct comprising an Ss2-ODD1 sequence.

BRIEF DESCRIPTION OF THE DRAWINGS

FIG. 1 shows conservation of functional amino acid residues in Ss2-ODD1, its close homologues from *Oryza sativa, Sorghum bicolor* and *Zea mays* and plant ferrous iron-dependent dioxygenases (SEQ ID NOS 11-61, respectively, in order of appearance). Numbering of residues was based on the isopenicillin N synthase (IPNS) protein from *Streptomyces jumonjinesis*. The alignment shows conserved residues (underlined) including the iron binding motif His-X-Asp(53-57)X-His (shaded) that is common to non-heme Fe(II) dependent dioxygenases (Kreisberg-Zakarin et al., *Antonie Van Leeuwenhoek* 75: 33-39, 1999). These conserved residues are presumed to be necessary for iron binding in the active site (Borovok et al., Biochemistry 35: 1981-1987, 1996). Ss, *Saccharum* species; Sb, *Sorghum bicolor*; Zm, *Zea mays*; ORYSA, *Oryza sativa*; ARATH, *Arabidopsis thaliana*; CUCMA, *Cucurbita maxima*; STRJU, *Streptomyces jumonjinensis*; PETHY, *Petunia hybrida*; GARPE, garden petunia;

2-ODD1, 2-oxoacid-dependent dioxygenase; GA2, Gibberellin 2β-Hydroxylases; GA20, Gibberellin 20-Oxidases; GA3, Gibberellin 3β-Hydroxylases; GA7, Gibberellin 7-Oxidases; A2, A2 gene; LDOX, leucoanthocyanidin dioxygenase; FLS, flavonol synthase; FL3H, Flavanone 3β-Hydroxylase; 2A6, 2A6 gene.

Figure 2:
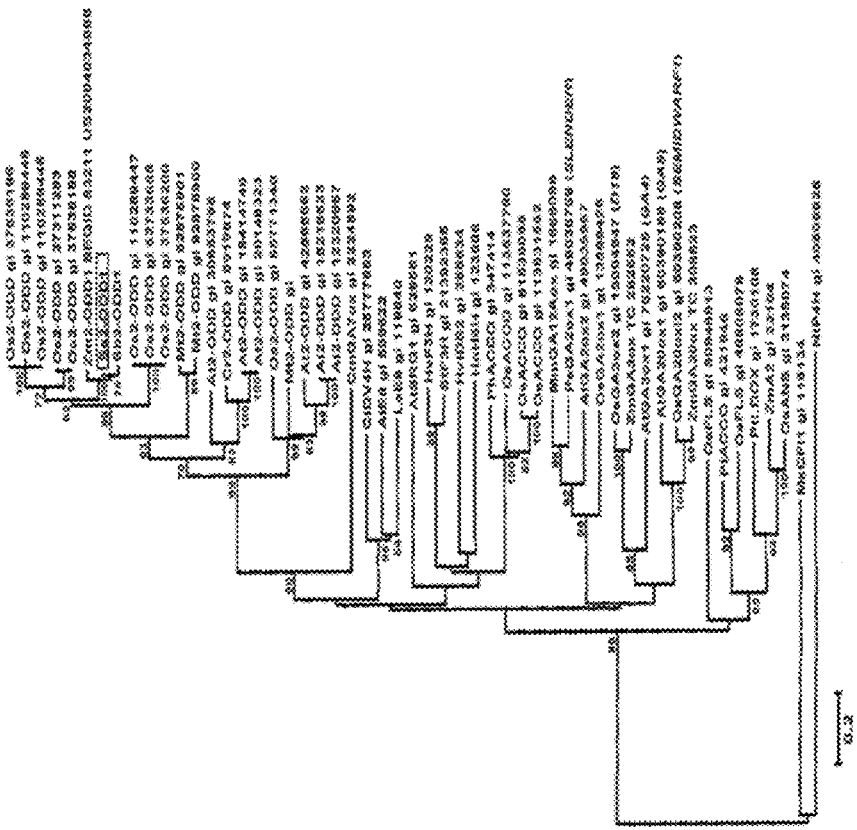

FIG. 2 shows phylogenetic analysis of higher plant 2-ODDS. Amino acid sequences of higher plant representatives of major 2-ODDS types were aligned with the Clustal algorithm using the BLOSUM matrix. Phylogenetic reconstructions were obtained in MEGA version 3.1 (Kumar et al., *Brief Bioinform*. 5: 150-163, 2004) by the Neighbor-Joining method (NJ) with robustness of nodes of the phylogenetic trees assessed by bootstrapping (1,000 resamplings). Bootstrap values larger than 50 are shown. GenBank gi or TIGR TC numbers are provided following sequence names. Ss2-ODD1 is boxed. Proteins with corresponding characterized gibberellic acid oxidase mutants of *Arabidopsis thaliana* (GA5, GA4), *Oryza sativa* (D18, SEMIDWARF1), and *Pisum sativum* (SLENDER) are indicated. Species and protein names are abbreviated as follows: At, *Arabidopsis thaliana*; Cm, *Cucurbita maxima*; Cr, *Capsella rubella*; Cro, *Catharanthus roseus*; Hv, *Hordeum vulgare*; Hn, *Hyoscyamus niger*; Le, *Lycopersicum esculentum*; Mm, *Marah macrocarpus*; Ms, *Medicago sativa*; Mt, *Medicago truncatula*; Nt; *Nicotiana tabacum*; Os, *Oryza sativa* (specifically, Os2-ODD gi62733655 (SEQ ID NO:64)); Ps, *Pisum sativum*; Pt, *Petunia×hybrida*; St, *Solanum tuberosum*; Sb, *Sorghum bicolor*; Ss, *Saccharum* species; Zm, *Zea mays* (specifically, Zm2-ODD1 SEQ ID 53211 US2004034888 (SEQ ID NO:63)). A2, protein encoded by the A2 locus that affects anthocyanin biosynthesis; ACCO, 1-aminocyclopropane-1-carboxylate oxidase; ANS, anthocyanidin synthase; CFI, chalcone-flavonone isomerase; DV4H, desacetoxyvindoline 4-hydroxylase; E8, 1-aminocyclopropane-1-carboxylate oxidase homolog (protein E8); F3H, flavonone-3-hydroxylase; FLS, flavonol synthase; GAoxi, gibberellic acid oxidase; H6H, hyoscyamine 6-dioxygenase; IDS2, iron deficiency specific-2; LDOX, leucoanthocyanidin dioxygenase; P4H, prolyl 4-hydroxylase; SRG1, encoded transcript expressed in growth-arrested *Arabidopsis thaliana* cells.

Figure 3:
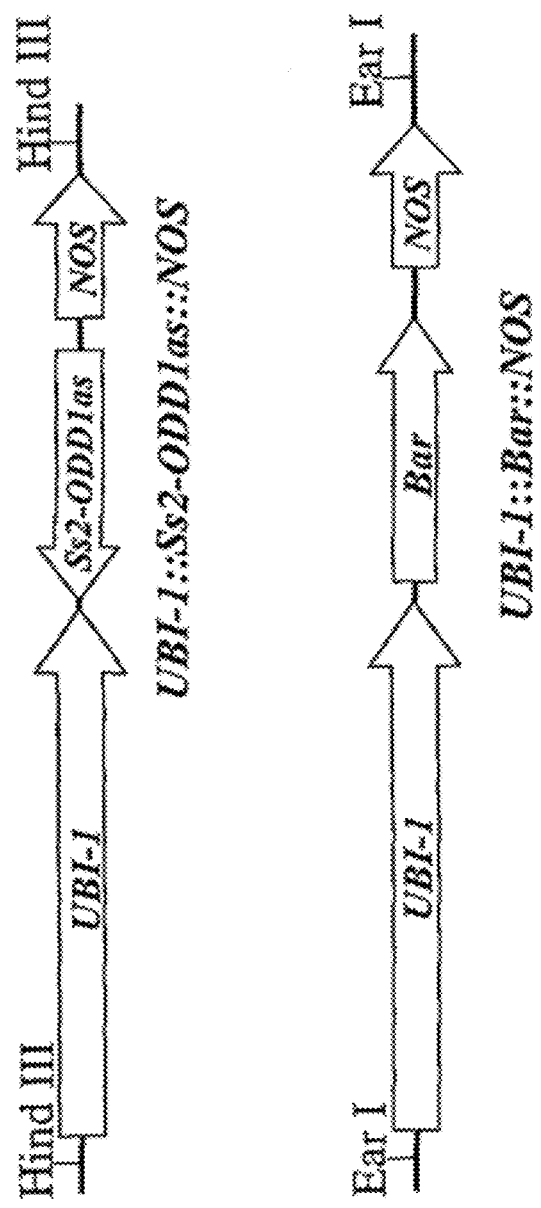

FIG. 3 shows schematic representation of UBI-1::Ss2-ODD1as::NOS and UBI-1::Bar::NOS cassettes. Endonucleases (EarI and HindIII) used for releasing cassettes from original cloning vectors are shown.

Figure 4:
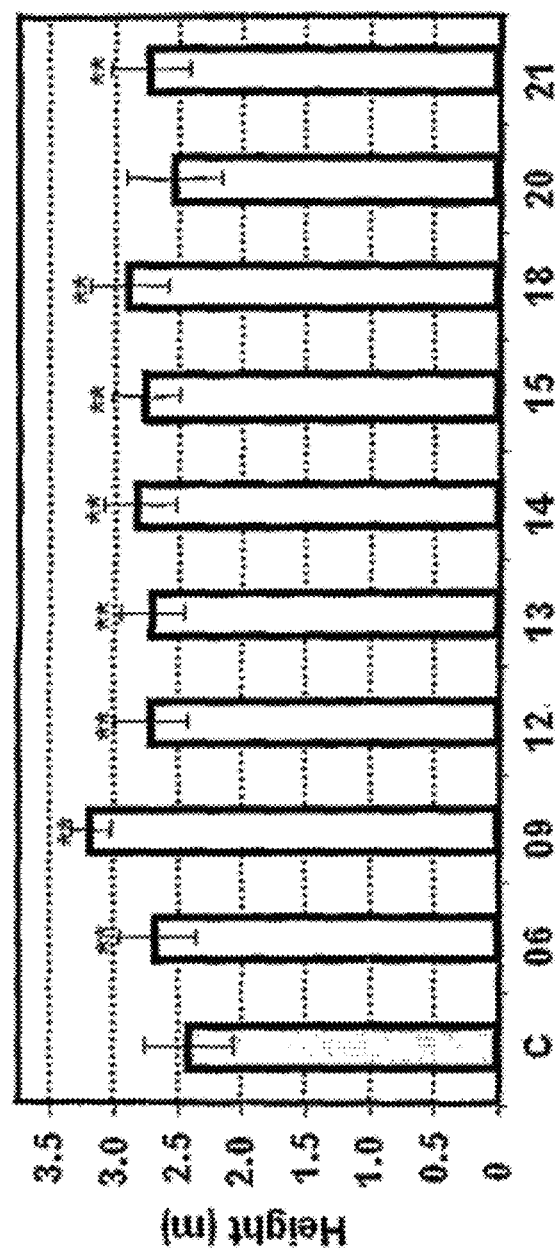

FIG. 4 shows height of selected UBI-1::Ss2-ODD1as::NOS events and non-transgenic control cultivar RB835486. Height of two stems was measured for each sample (n=12) after removal of the stalk apical sections. Double asterisks indicate events significantly different from the cultivar RB835486 non-transgenic control (C) as determined by the Dunnett's method at the 99% confidence level. Error bars indicate standard deviation of the mean.

Figure 5:
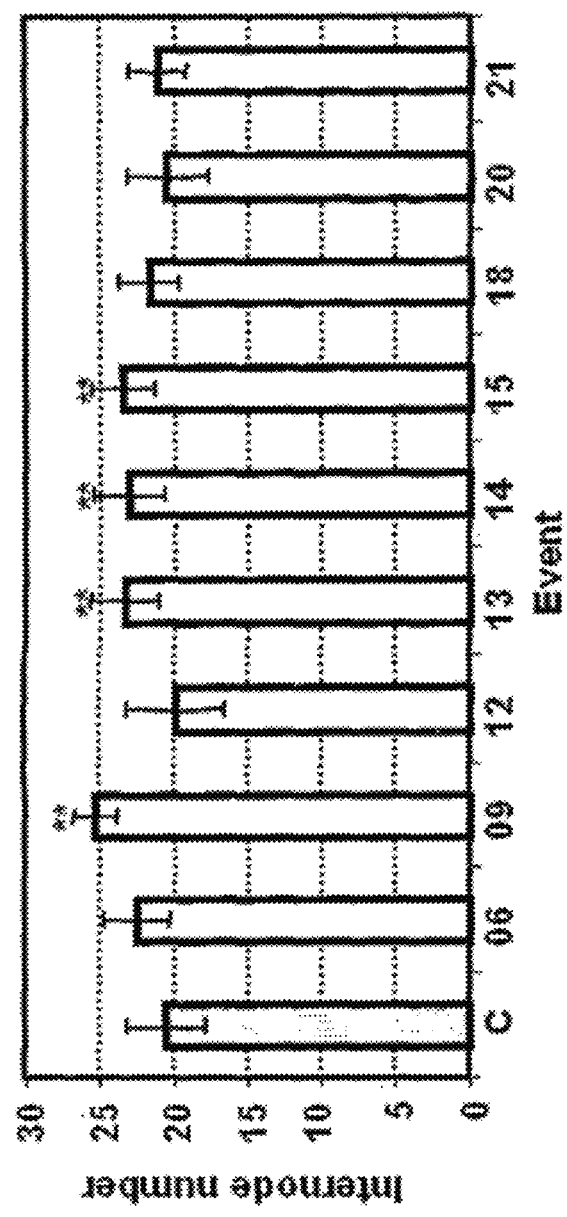

FIG. 5 shows internode number of selected UBI-1::Ss2-ODD1as::NOS events and non-transgenic control cultivar RB835486. Internode number of two stalks was determined for each sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 6:
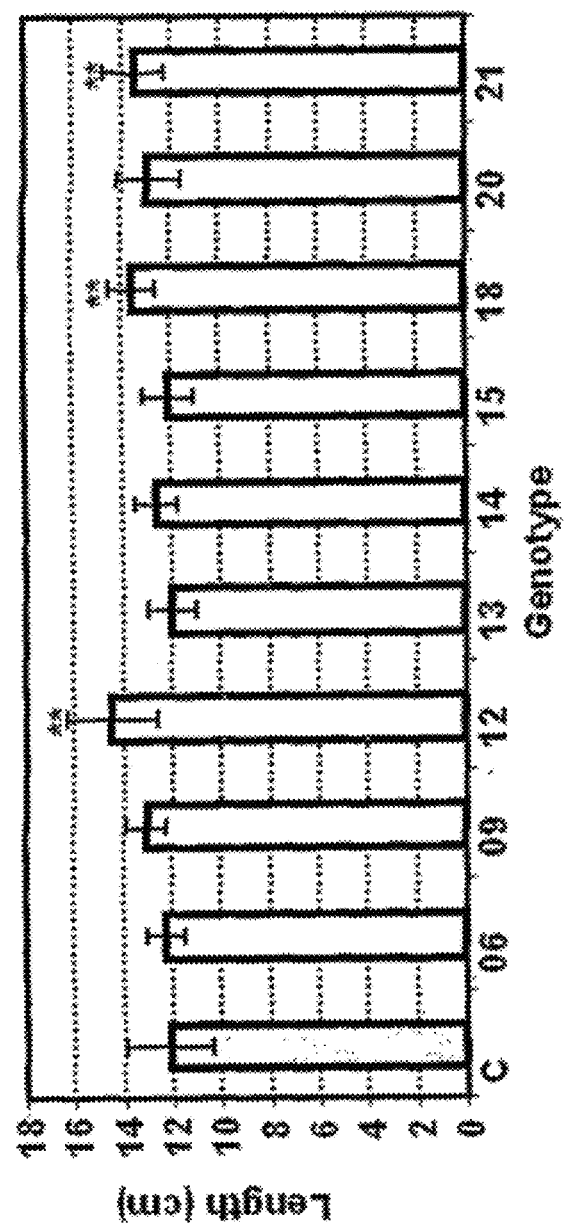

FIG. 6 shows average internode length of selected UBI-1::Ss2-ODD1as::NOS events and non-transgenic control cultivar RB835486. Length of all internodes of two stalks was measured for each sample (n=12) after removal of the apical part. Double asterisks indicate events significantly different from the cultivar RB835486 non-transgenic control (C) as determined by the Dunnett's method at the 99% confidence level. Error bars indicate standard deviation of the mean.

Figure 7:
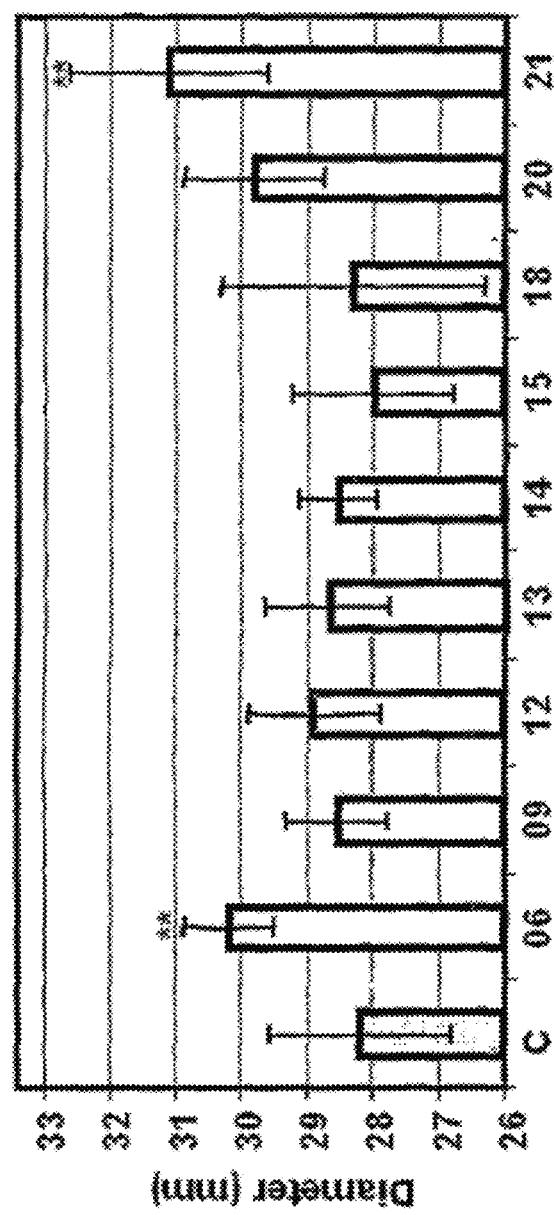

FIG. 7 shows average internode diameter of selected UBI-1::Ss2-ODD1as::NOS events and non-transgenic control cultivar RB835486. Internode diameter of two stalks was measured for each sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 8:
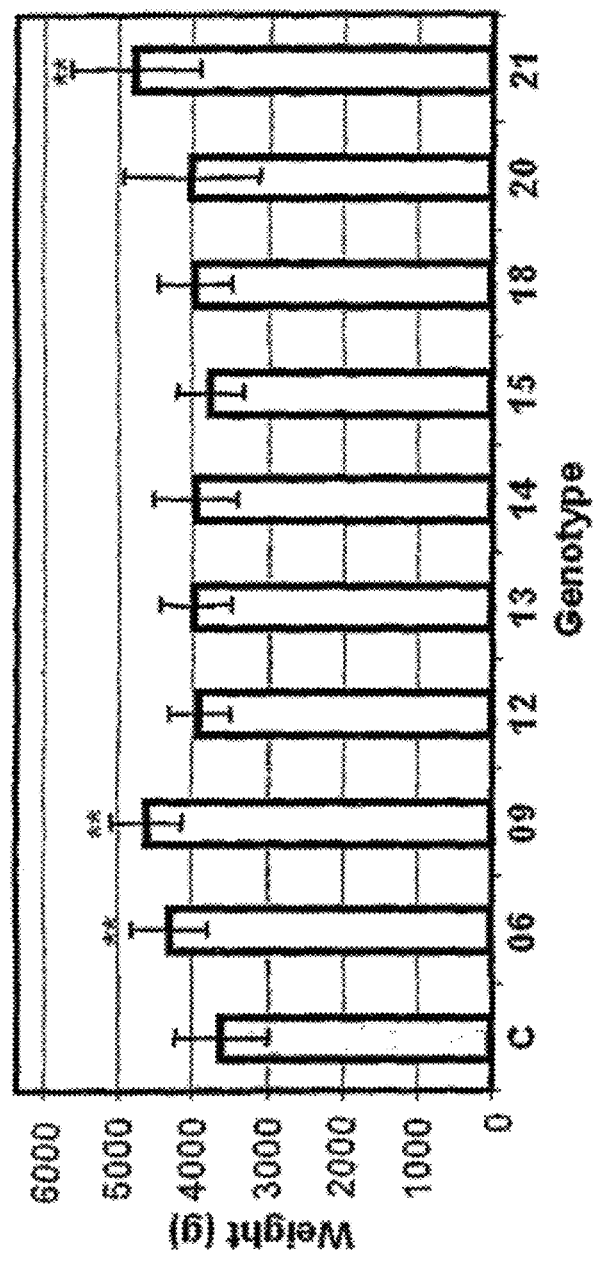

FIG. 8 shows stalk fresh weight of selected UBI-1::Ss2-ODD1as::NOS events and non-transgenic control cultivar RB835486. Fresh weight of two combined stalks was measured for each sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 9:
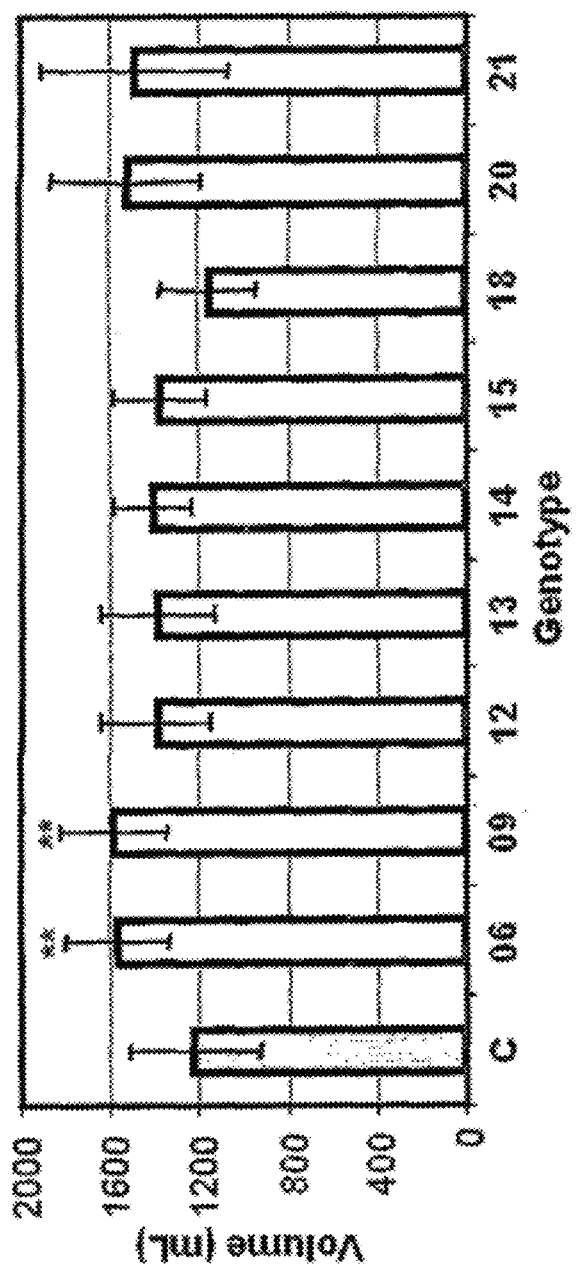

FIG. 9 shows juice volume of selected UBI-1::Ss2-ODD1as::NOS events and non-transgenic control cultivar RB835486. Juice volume extracted from two combined stalks was measured for sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 10:
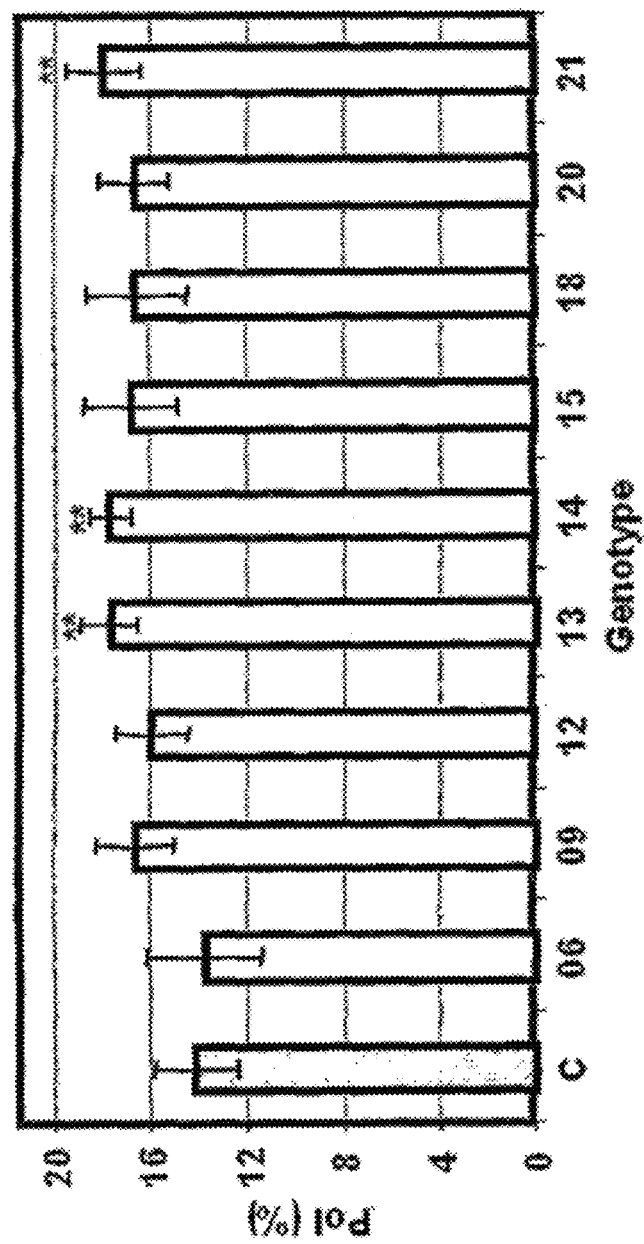

FIG. 10 shows POL of selected UBI-1::Ss2-ODD1as::NOS events and non-transgenic control cultivar RB835486. POL of juice extracted from two combined stalks was measured for each sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 11:
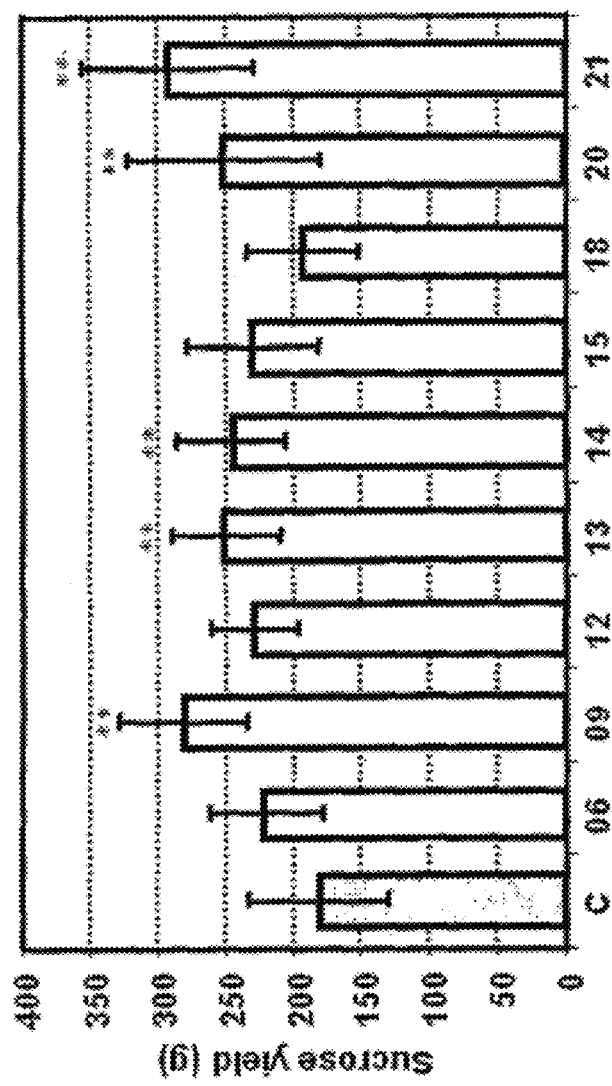

FIG. 11 shows sucrose yield of selected UBI-1::Ss2-ODD1as::NOS events and non-transgenic control cultivar RB835486. Sucrose yield was calculated as a product of total juice volume and its sucrose concentration from two combined stalks for each sample (n=12) after removal of the apical section, Double asterisks indicate events significantly different from the cultivar RB835486 non-transgenic control (C) as determined by the Dunnett's method at the 99% confidence level. Error bars indicate standard deviation of the mean.

Figure 12:
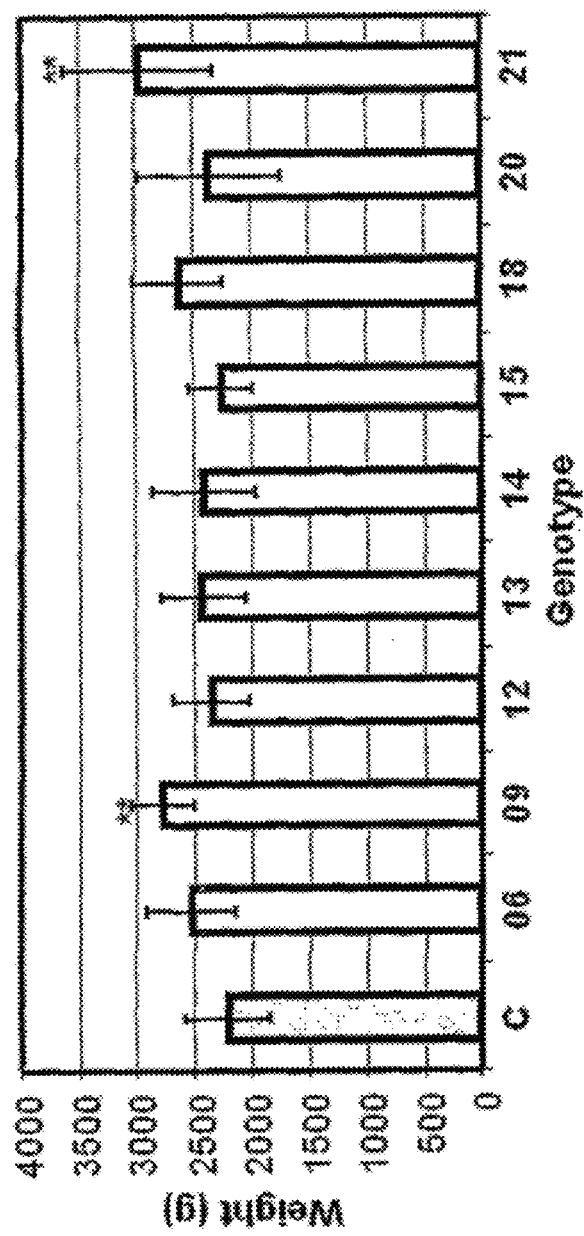

FIG. 12 shows bagasse fresh weight of selected UBI-1::Ss2-ODD1as::NOS events and non-transgenic control cultivar RB835486. Bagasse fresh weight of two combined stalks was measured for each sample (n=12) after removal of the apical section. Double asterisks indicate events significantly different from the cultivar RB835486 non-transgenic control (C) as determined by the Dunnett's method at the 99% confidence level. Error bars indicate standard deviation of the mean.

Figure 13:
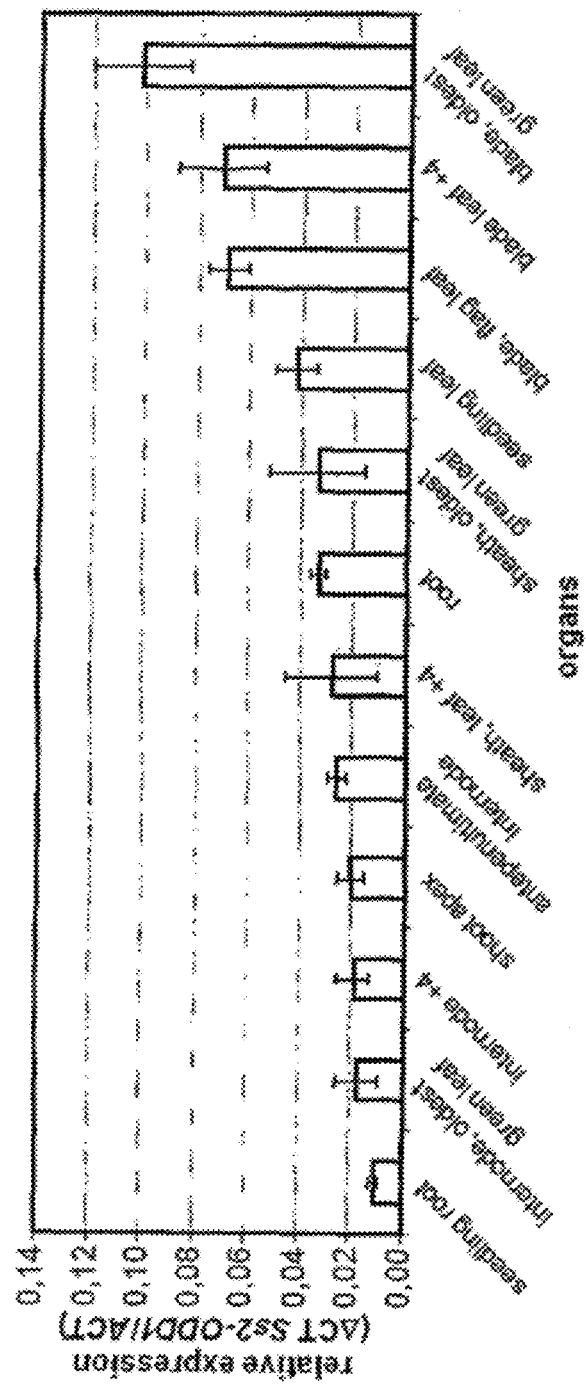

FIG. 13 shows expression of Ss2-ODD1 transcripts in wild-type sugarcane organs measured by quantitative reverse transcription-polymerase chain reaction (qRT-PCR). Quantitative reverse transcription-polymerase chain reaction (qRT-PCR) was performed using RNA isolated from different organs of wild-type sugarcane plants (cultivar RB835486). Abundance of Ss2-ODD1 transcripts relative to those of ACTIN (ACT) are expressed as ΔCT values. Bars indicate mean values from three independent replicates. Error bars indicate standard deviation of the mean.

Figure 14:
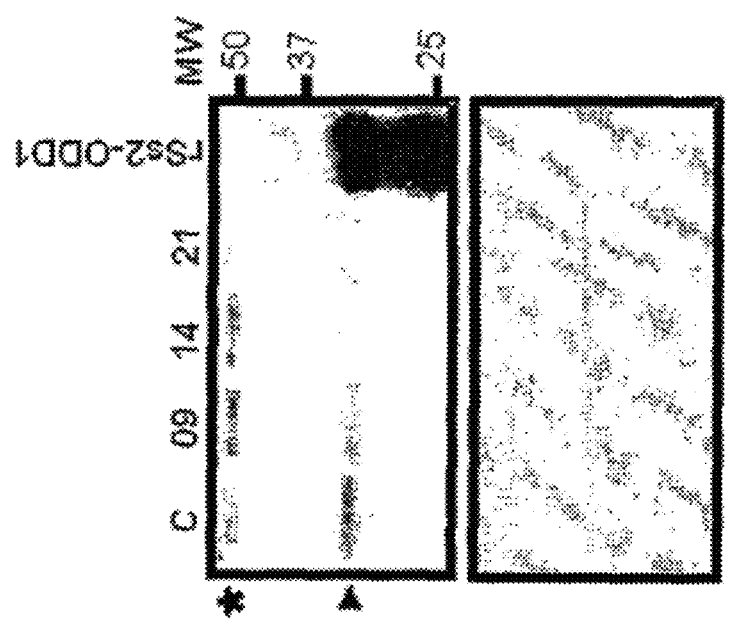

FIG. 14 shows Ss2-ODD1 protein levels in the leaf +4 of selected UBI-1::Ss2-ODD1as::NOS events and wild-type sugarcane cultivar RB835486 controls. Extracts were prepared from blades of leaf +4 harvested from cultivar RB835486 wild-type plants (C) and events 09, 14 and 21. Leaf protein extracts (50 μg) along with 0.5 ng of recombinant Ss2-ODD1 (rSs2-ODD1) were separated by SDS-PAGE. Immunoblotting was performed with Ss2-ODD1 affinity-purified antibodies (upper panel). Arrowhead indicates Ss2-ODD1 protein. Asterisk indicates a non-specific cross-reacting polypeptide in leaf extracts shown as loading control. Molecular weights are shown at the right (MW) expressed in kDa. The gel stained with Coomassie Blue after transfer is shown as a loading control (bottom panel).

DETAILED DESCRIPTION OF THE INVENTION

The present invention relates to methodology and constructs for manipulating a dioxygenase enzyme in planta, thereby modifying plant architecture and enhancing plant biomass and/or sucrose yield. Dioxygenases are iron-containing, non-heme enzymes that are involved in the biosynthesis of many compounds, including penicillin, cephalosporin, cephamycin, clavam, carnitine and collagen biosynthesis (Prescott and Lloyd, *Nat. Prod. Rep.*, 17: 367-383, 2000). Also, some dioxygenases have long been described to oxidize several amino acids residues in various protein targets to facilitate protein folding. Modifications in amino acid oxidation permit regulatory and structural mechanisms (Ozer and Bruick, *Nat Chem. Biol.*, 3: 144-153, 2007). In plants particularly, various dioxygenases play crucial roles in the biosynthesis of signaling compounds such as abscisic acid, gibberellins, and ethylene and also of secondary metabolites, notably flavonoids and alkaloids. Surveys of reactions catalyzed by dioxygenases are provided by several articles and references therein (Prescott and John, *Annu. Rev. Plant Physiol. Plant Mol. Biol.*, 47:245-271, 1996; Prescott and Lloyd, *Nat. Prod. Rep.*, 17:367-383, 2000; Turnbull et al., *J. Biol. Chem.* 279: 1206-1216, 2004; Ozer and Bruick, *Nat. Chem. Biol.*, 3: 144-153, 2007).

Plant dioxygenases fall into two classes: lipoxygenases and 2-oxoglutarate-dependent dioxygenases (2-ODDs) that catalyze hydroxylation, epoxidation, and desaturation reactions. Members of latter frequently catalyze more than one type of reaction in successive steps in a biosynthetic pathway. Enzymes in 2-ODDs group show an absolute requirement for 2-oxoglutarate as a co-substrate. All 2-ODDs are soluble enzymes that require $Fe^{2+}$ and ascorbate for optimal substrate conversion in vitro. Some enzymes have an absolute requirement for ascorbate, but many do not. Often the role of ascorbate is undefined and is likely to be indirect and unrelated to the reaction mechanism.

Sequences of 2-ODDS are characterized by conserved residues mainly clustered in the carboxy-terminal half of the protein. Three-dimensional structures have been published for the microbial 2-ODD, isopenicillin N synthase (IPNS; Kreisberg-Zakarin et al., *Antonie van Leeuwenhoek*, 75: 33-39, 1999). Although IPNS shows relatively low sequence identity to plant 2-ODDS, it shares a number of conserved residues/motifs and structural elements and has been proposed as a model for the structure of plant 2-ODDs. The structure show that the catalytic core of the INPS consist of a double-stranded β-helix (DSBH) fold containing a HX[DE] dyad (where X is any amino acid) and a conserved carboxy-terminal histidine which together chelate a single iron atom (Kreisberg-Zakarin et al., *Antonie van Leeuwenhoek*, 75: 33-39, 1999). The conserved portion of 2-ODD super-family proteins comprises the core DSBH which is arranged in two sheets in a jelly-roll topology, a comparatively rare structure in enzymes more commonly found in viral capsid proteins.

Alignments to compare primary amino acid sequences of a large group of non-heme Fe(II)-dependent dioxygenases, all of which activate molecular oxygen and carry out diverse reactions such as aliphatic hydroxylations, desaturations and cyelizations, were analyze (Kreisberg-Zakarin et al., *Antonie van Leeuwenhoek*, 75: 33-39, 1999). Sequence analysis of some 52 members of this class of enzymes established that five residues alone are conserved throughout—Gly41, His212, Asp214, His268 and Arg277, numbering according to *S. jumonjinensis* IPNS (Borovok et al., *Biochemistry*, 35: 1981-1987, 1996). Biochemical analysis revealed that mutant enzymes in His212, Asp214 and His268 have no activity in vitro (Tan and Sim, *J. Biol. Chem.*, 271: 889-894, 1996; Loke et al., *FEMS Microbiol. Lett.*, 157: 137-140, 1997), implying that the two conserved histidines and aspartic acids are essential for IPNS activity. A more extensive analysis comprising 139 non-redundant non-heme, Fe(II)-dependent dioxygenases revealed that both the two histidines and the aspartic acid and the glycine are fully conserved (Kreisberg-Zakarin et al., *Antonie van Leeuwenhoek*, 75: 33-39, 1999). This analysis was used to define a sequence motif that is common to all the non-heme Fe(II) dependent dioxygenases, His-X-Asp(53-57)X-His, which is presumed to be necessary for binding of the iron in the active site (Borovok et al., *Biochemistry*, 35: 1981-1987, 1996). No role so far has been ascribed to the Gly41.

Against this background, the present invention describes a method for modifying plant architecture and enhancing plant biomass and/or sucrose yield through the down-regulation of a dioxygenase-encoding gene.

All technical terms employed in this description are in common use in the fields of biochemistry, molecular biology, immunology and agriculture; hence, they are easily understood by a person skilled in the art to which the present invention belongs. These technical terms can be found, for instance, in: MOLECULAR CLONING: A LABORATORY MANUAL, $3^{rd}$ ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; Harlow and Lane (ANTIBODIES: A LABORATORY MANUAL, Cold Spring Harbor Laboratory Press, Cold Spring Harbor, N.Y., 1988. Methodology involving plant biology techniques is described herein and is described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, e.g., in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage & Caruthers, *Tetra. Letts.* 22: 1859-1862 (1981), and Matteucci & Caruthers, *J. Am. Chem. Soc.* 103: 3185 (1981).

Restriction enzyme digestion, phosphorylation, ligation and transformation were performed as described in Sambrook et al., MOLECULAR CLONING: A LABORATORY MANUAL, 2$^{nd}$ ed. (1989), Cold Spring Harbor Laboratory Press, unless otherwise specified. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.), unless otherwise specified.

The terms "encoding" and "coding" refer to the process by which a polynucleotide, through the mechanisms of transcription and translation, provides information to a cell from which a series of amino acids can be assembled into a specific polypeptide. Because of the degeneracy of the genetic code, certain base changes in DNA sequence do not change the amino acid sequence of a protein.

The term "expression" denotes the production of the polypeptide encoded by a polynucleotide. Alternatively or additionally, "expression" denotes the combination of intracellular processes, including transcription and translation, undergone by a coding DNA molecule such as a structural gene to produce a polypeptide. "Down-regulation" and "suppression" are used synonymously to indicate that the expression of a particular gene sequence in a cell or plant has been reduced relative to a control cell or plant.

The phrase "altered expression" in reference to a polynucleotide indicates that the pattern of expression in, e.g., a transgenic plant or plant tissue, is different from the expression pattern in a wild-type plant of the same species. Thus, the polynucleotide of interest is expressed in a cell or tissue type other than a cell or tissue type in which the sequence is expressed in the wild type plant, or by expression at a time other than at the time the sequence is expressed in the wild type plant, or by a response to different inducible agents, such as hormones or environmental signals, or at different expression levels, compared with those found in a wild type plant. The resulting expression pattern can be transient or stable, constitutive or inducible. With reference to a polypeptide, "altered expression" further may relate to altered activity levels resulting either from altered protein levels or from interactions of the polypeptides with exogenous or endogenous modulators, or from interactions with factors or as a result of the chemical modification of the polypeptides.

The terms "exogenous nucleic acid" and "heterologous nucleic acid" are used interchangeably and refer to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, the term "endogenous nucleic acid" refers to a nucleic acid, gene, polynucleotide, DNA, RNA, mRNA, or cDNA molecule that is present in a plant or organism that is to be genetically engineered. An endogenous sequence is "native" to, i.e., indigenous to, the plant or organism that is to be genetically engineered.

The phrase "homologous sequences" refers to polynucleotide or polypeptide sequences that are similar due to common ancestry and sequence conservation. Homologous sequences may be "orthologous," if they were separated by a speciation event, or "paralogous," if they were separated by a gene duplication event.

The phrase "functional homolog" refers to a polynucleotide or polypeptide sequences that are similar due to common ancestry and sequence conservation and have identical or similar function at the catalytic, cellular, or organismal levels.

Dioxygenase Sequences

Dioxygenase-encoding genes have been identified in several plant families, exemplified by Poaceae members such as sugarcane and sorghum. In accordance with the present invention provides, 2-oxoglutarate-dependent dioxygenase (2-ODD) sequences can be employed, as described above, to modify plant architecture and to enhance biomass and/or sucrose yield.

In the context of the present invention, "Ss-2ODD1" refers to a plant enzyme for which decreased protein levels and/or activity results in plants with modified architecture and enhanced biomass and/or sucrose yield. In the context of the present invention, "Ss-2ODD1" refers to a plant enzyme whose decreased protein levels and/or suppression of activity confers modified plant architecture and increased sucrose and/or biomass, as well as possesses dioxygenase activity having the potential to catalyze at least one of the following reactions:

(a) activation of molecular oxygen and catalysis of substrate conversions, including hydroxylation, desaturation, cyclization, and epoxidation, with or without 2-oxoglutarate requirement as a co-substrate;

(b) oxidation of biomolecules (metabolites and macromolecules) with or without an ascorbate requeriment as cofactor;

(c) catalysis of oxygen incorporation from $O_2$ in organic (metabolites and macromolecules) substrates;

(d) biosynthesis or degradation of plant signaling compounds such abscisic acid, gibberellins and ethylene; and (e) biosynthesis or degradation of secondary metabolites, notably flavonoids and alkaloids.

The polynucleotides of the invention encode polypeptides characterized by a high sequence identity to 2-oxoglutarate-dependent dioxygenase (2-ODD) polypeptides. While exemplary 2-ODD sequences are derived from Poaceae, such as the *Saccharum* spp. 2-ODD (Ss2-ODD1), functional homologs from other plant families can be used to produce plants with modified plant architecture and at least one of enhanced biomass and increased sucrose yield. As shown in FIG. 2, 2-ODD sequences have been identified in several plant families: Poaceae (e.g., sugarcane and sorghum), Cucurbitaceae (e.g., pumpkin and winter squash), Brassicaceae (e.g., *Arabidopsis*), Solanaceae (e.g., tobacco and tomato), Leguminosae (e.g., garden pea), and Apocynaceae (e.g., Madagascar periwinkle), inter alia. It is expected that plant 2-ODD genes from other plant families catalyze the same reactions affected by the Ss2-ODD1 enzyme (SEQ ID NO: 2) that illustrative SEQ ID NO: 1 encodes; hence, a reduced expression of such genes should lead to the phenotypes described above and illustrated by plants described in the examples, infra.

Furthermore, common genetic mechanisms control vegetative architecture within the Poaceae family and even across dicot and monocot species. For example, see Doust, *Ann. Bot.* 100: 941-50, 2007, and publications cited therein. Accordingly, the identification and isolation from different families of functional homologs that control plant architecture and biomass accumulation should permit the modification of these characteristics in a wide range of plants, pursuant to the present invention.

Additional 2-ODD sequences can be identified and functionally annotated by sequence comparison. Thus, the skilled person can readily identify a functionally related Ss2-ODD1 sequence in a suitable database, such as GenBank, using publicly available sequence-analysis programs and parameters. Sequences initially identified as 2-ODD may be characterized further, thereby to identify sequences that comprise specified sequence strings corresponding to sequence motifs present in families of known dioxygenases. Alternatively, screening cDNA libraries or genomic libraries, employing suitable hybridization probes and conditions, should lead to the identification of functionally related Ss2-ODD1 sequences. It is appreciated in the field as well that sequences with reduced levels of identity also can be isolated with the aid of (degenerate) oligonucleotides and PCR-based methodology.

Via the techniques described above, therefore, a sequence can be identified and functionally annotated as belonging to the Ss2-ODD1 family. By the same token, "Ss2-ODD1 DNA sequence" in this description refers to any nucleic acid molecule with a nucleotide sequence capable of hybridizing under stringent or highly stringent conditions with the sequence set forth in SEQ ID NO: 1, and encodes an Ss2-ODD1 enzyme as defined above. The category denoted by the term also encompasses sequences which cross-hybridize with SEQ ID NO: 1, preferably having at least 40%, preferably at least 60%, especially preferably at least 80% and particularly preferably at least 90%, 91%, 92%, 93%, 94%, 95%, 96%, 97%, 98%, 99%, or 99.9% identity with the Ss2-ODD1 nucleotide sequence shown in SEQ ID NO: 1. The nucleotide sequence of the invention may encode a protein that is homologous to the predicted gene product set forth in SEQ ID NO: 2.

The phrase "stringent conditions" here connotes parameters with which the art is familiar. Single-stranded polynucleotides hybridize when they associate based on a variety of well-characterized physicochemical forces, such as hydrogen bonding, solvent exclusion, and base stacking. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number).

For hybridization of complementary nucleic acids, which have more than 100 complementary residues, on a filter in a Southern or Northern blot, "stringent" hybridization conditions are exemplified by a temperature that is about 5° C. to 20° C. lower than the thermal melting point (Tm) for the specific sequence, at a defined ionic strength and pH. The Tm is the temperature, under defined ionic strength and pH, at which 50% of the target sequence hybridizes to a perfectly matched probe. Nucleic acid molecules that hybridize under stringent conditions typically will hybridize to a probe based on either the entire cDNA or selected portions. More preferably, "stringent conditions" here refers to parameters with which the art is familiar, such as hybridization in 3.5×SSC, 1×Denhardt's solution, 25 mM sodium phosphate buffer (pH 7.0), 0.5% SDS, and 2 mM EDTA for 18 hours at 65° C., followed by four washes of the filter, at 65° C. for 20 minutes, in 2×SSC and 0.1% SDS, and a final wash for up to 20 minutes in 0.5×SSC and 0.1% SDS or 0.3×SSC and 0.1% SDS for greater stringency, and 0.1×SSC and 0.1% SDS for even greater stringency. Other conditions may be substituted, as long as the degree of stringency is equal to that provided herein, using a 0.5×SSC final wash. For identification of less closely related homologues washes can be performed at a lower temperature, e.g., 50° C. In general, stringency is increased by raising the wash temperature and/or decreasing the concentration of SSC.

The invention provides nucleic acid molecules comprising the nucleotide sequence of SEQ ID NO: 1, encoding an amino acid sequence set forth in SEQ ID NO: 2. It is understood that the protein of the invention encompasses amino acid substitutions, additions, and deletions that do not alter the function of the enzyme. For example, substitutions, deletions and insertions introduced into the inventive sequences are also embraced by the invention. Such sequence modifications can be engineered into a sequence by site-directed mutagenesis or by other methods known in the art. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding an ODD1 polypeptide, such as the Ss2-ODD1, should not place the sequence out of reading frame and should not create complementary regions that could produce secondary mRNA structure. Preferably, the polypeptide encoded by the DNA performs the desired function.

Dioxygenases sequences that are homologous to the listed sequences will typically share at least about 40% amino acid sequence identity. More closely related dioxygenases amino acid sequences share at least about 50%, about 60%, about 65%, about 70%, about 75% or about 80% or about 90% or about 95%, 96%, 97%, 98% or even 99.9% amino acid sequence identity with the listed sequences. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences. The degeneracy of the genetic code enables major variations in the nucleotide sequence of a polynucleotide while maintaining the amino acid sequence of the encoded protein.

Accordingly, the present invention embraces any nucleic acid, gene, polynucleotide, DNA, RNA, mRNA, or cDNA molecule that is isolated from a plant that encodes a 2-ODD polypeptide and whose suppression modifies plant architecture and increases plant biomass and/or sucrose yield. The DNA or RNA may be double-stranded or single-stranded. Single-stranded DNA may be the coding strand, also known as the sense strand, or it may be the non-coding strand, also called the anti-sense strand.

It will readily be appreciated by those of skill in the art, that any of a variety of polynucleotide sequences are capable of encoding 2-ODD polypeptides. Due to the degeneracy of the genetic code, many different polynucleotides can encode identical and/or substantially similar polypeptides in addition to those sequences illustrated in the Sequence Listing.

The term "variant" is a nucleotide or amino acid sequence that deviates from the standard, or given, nucleotide or amino acid sequence of a particular gene or protein. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software. "Variant" may also refer to a "shuffled gene,"

as described, for example, in U.S. Pat. No. 6,506,603, U.S. Pat. No. 6,132,970, U.S. Pat. No. 6,165,793 and U.S. Pat. No. 6,117,679.

Also contemplated are fragments and domains, referred herein as oligonucleotides, which hybridize under at least stringent or highly stringent conditions to a polynucleotide sequence described above. The oligonucleotides are useful as primers, probes, and the like. An oligonucleotide suitable for use as probes, primes, sense and antisense agents is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods.

The term "fragment" or "domain," with respect to a polypeptide, refers to a subsequence of the polypeptide. In some cases, the fragment or domain is a subsequence of the polypeptide that performs at least one biological function of the intact polypeptide in substantially the same manner, or to a similar extent, as does the intact polypeptide. For example, a polypeptide fragment can comprise a recognizable structural motif or functional domain such as a DNA binding domain that binds to a DNA promoter region, an activation domain or a domain for protein-protein interactions. Fragments can vary in size from as few as 6 amino acids to the full length of the intact polypeptide, but are preferably at least about 30 amino acids in length and more preferably at least about 60 amino acids in length.

As used herein, "Ss2-ODD1 DNA sequence" is understood to mean that the Ss2-ODD1 gene includes the sequence set forth in SEQ ID NO: 1, as well as nucleic acid molecules comprised of variants of SEQ ID NO: 1, with one or more bases deleted, substituted, inserted, or added, which variant codes for a polypeptide with at least 40% amino acid sequence identity. Accordingly, sequences having "base sequences with one or more bases deleted, substituted, inserted, or added" retain physiological activity even when the encoded amino acid sequence has one or more amino acids substituted, deleted, inserted, or added. Additionally, multiple forms of Ss2-ODD1 enzyme may exist, which may be due to post-translational modification of the polypeptide or to multiple forms of the Ss2-ODD1 gene. Nucleotide sequences that have such modifications and that code for a dioxygenase enzyme are included within the scope of the present invention.

For example, the poly A tail or 5'- or 3'-end, nontranslation regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of dioxygenase enzyme activity. A modified DNA in this context can be obtained by modifying the DNA base sequences of the invention so that amino acids at specific sites are substituted, deleted, inserted, or added by site-specific mutagenesis, for example, Zoller & Smith, *Nucleic Acid Res.* 10: 6487-500, 1982.

Unless otherwise indicated, all nucleotide sequences determined by sequencing a DNA molecule herein were determined using an automated DNA sequencer, such as the Model 373 from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Nucleic Acid Constructs

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence has been inserted, in a forward or reverse orientation. In a preferred embodiment, the construct further comprises regulatory sequences, including, for example, a promoter operably linked to the sequence. Large numbers of suitable vectors and promoters are known and are commercially available.

Recombinant nucleic acid constructs may be made using standard techniques. For example, a nucleotide sequence for transcription may be obtained by treating a vector containing said sequence with restriction enzymes to cut out the appropriate segment. The nucleotide sequence for transcription may also be generated by annealing and ligating synthetic oligonucleotides or by using synthetic oligonucleotides in a polymerase chain reaction (PCR) to give suitable restriction sites at each end. The nucleotide sequence then is cloned into a vector containing suitable regulatory elements, such as upstream promoter and downstream terminator sequences.

Typically, plant transformation vectors include one or more cloned plant coding sequence (genomic or cDNA) under the transcriptional control of 5' and 3' regulatory sequences and a selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Suitable constitutive plant promoters which can be useful for expressing the ODD1 sequences of the invention include but are not limited to: the cauliflower mosaic virus (CaMV) 35S promoter and the maize polyubiquitin promoter, which confer constitutive, high-level expression in most plant tissues (see, e.g., U.S. Pat. No. 5,510,474; Odell et al., *Nature* 313: 810-812, 1985); the nopaline synthase promoter (An et al., *Plant Physiol.* 88: 547-552, 1988); and the octopine synthase promoter (Fromm et al., *Plant Cell* 1: 977-984, 1989); as well as tissue-specific, tissue-preferred, cell type-specific, and inducible promoters. For example, in sugarcane, sucrose produced in the leaves accumulates in the "internode," which refers to the portion of the shoot axis between two nodes, it may be advantageous to use an internode-specific promoter.

The vector may also contain termination sequences, which are positioned downstream of the nucleic acid molecules of the invention, such that transcription of mRNA is terminated, and polyA sequences added. Exemplary terminators are the cauliflower mosaic virus (CaMV) 35S terminator and the nopaline synthase gene (NOS) terminator.

Expression vectors may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3% O-phosphotranserase (kanamycin, neomycin and G418 resistance). These markers may include resistance to G418, hygromycin, bleomycin, kanamycin, and gentamicin. The construct also may contain the selectable marker gene Bar, which confers resistance to herbicidal phosphinothricin analogs like ammonium gluphosinate. Thompson et al., *EMBO J.* 6: 2519-23 (1987). Other suitable selection markers are known as well.

Visible markers such as green florescent protein (GFP) may be used. Methods for identifying or selecting transformed plants based on the control of cell division have also been described. See John and Van Mellaert, WO 2000/052168, and Fabijansk et al., WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Methods for Altering the Expression of Polynucleotide and Polypeptide Sequences

In an aspect of the invention, plant biomass and/or sucrose yield are enhanced by down-regulating the expression of the polynucleotide sequences of the present invention. Various methods for post-transcriptional gene silencing (PTGS) are well known in the art and may be used in the present invention.

For example, a reduction or elimination of expression (i.e., a "knock-out") of the sequences of the present invention in a transgenic plant, e.g., to modify a plant trait, can be obtained by introducing an antisense construct corresponding to the polypeptide of interest as a cDNA. For antisense suppression, the polynucleotide sequence or homologue cDNA is arranged in reverse orientation (with respect to the coding sequence) relative to the promoter sequence in the expression vector. The introduced sequence need not be the full-length cDNA or gene, and need not be identical to the cDNA or gene found in the plant type to be transformed. Typically, the antisense sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-unstranslated region of the mRNA.

The particular antisense sequence and the length of the antisense sequence will vary, depending, for example, upon the degree of inhibition desired and the stability of the antisense sequence. Thus, where the introduced sequence is of shorter length, a higher degree of identity to the endogenous Ss2-ODD1 sequence will be needed for effective antisense suppression. While antisense sequences of various lengths can be utilized, preferably the introduced antisense sequence in the vector will be from at least 13 to about 15 nucleotides in length, at least 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or even the entire length of the sequence to be down-regulated. In addition, the sequences may be extended or shortened on the 3' or 5' ends thereof. Generally available techniques and the information provided in this specification can guide the selection of appropriate Ss2-ODD1-encoding antisense sequences. With reference to SEQ ID NO: 1 herein, an oligonucleotide of the invention may be a continuous fragment of an Ss2-ODD1 cDNA sequence in antisense orientation, of any length that is sufficient to achieve the desired effects when transformed into a recipient plant cell.

The present invention contemplates sense co-suppression of an Ss2-ODD1-encoding sequence. Sense polynucleotides employed in carrying out the present invention are of a length sufficient to suppress, when expressed in a plant cell, the native expression of the plant Ss2-ODD1 protein in that plant cell. Such sense polynucleotides may be essentially an entire genomic or complementary nucleic acid encoding the Ss2-ODD1 enzyme, or a fragment thereof, with such fragments typically being at least 15 nucleotides in length. Techniques are generally available for ascertaining the length of sense DNA that results in suppression of the expression of a native gene in a cell.

In an alternate embodiment of the present invention, plant cells are transformed with a nucleic acid construct containing a polynucleotide segment encoding an enzymatic RNA molecule (a "ribozyme"), which enzymatic RNA molecule is directed against (i.e., cleaves) the mRNA transcript of DNA encoding Ss2-ODD1, as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif.

Ribozyme cleavage sites within an RNA target may initially be identified by scanning the target molecule for ribozyme cleavage sites (e.g., GUA, GUU or GUC sequences). Once identified, short RNA sequences of 15, 20, 30, or more ribonucleotides corresponding to the region of the target gene containing the cleavage site may be evaluated for predicted structural features.

The suitability of candidate targets also may be evaluated by testing their accessibility to hybridization with complimentary oligonucleotides, using ribonuclease protection assays as are known in the art. DNA encoding enzymatic RNA molecules may be produced in accordance with known techniques. For example, see U.S. Pat. No. 4,987,071, U.S. Pat. No. 5,559,021, U.S. Pat. No. 5,589,367, U.S. Pat. No. 5,583,032, U.S. Pat. No. 5,580,967, No. 5,595,877, U.S. Pat. No. 5,591,601, and U.S. Pat. No. 5,622,854.

Production of such an enzymatic RNA molecule in a plant cell and disruption of Ss2-ODD1 protein production reduces protein activity in plant cells, in essentially the same manner as production of an antisense RNA molecule; that is, by disrupting translation of mRNA in the cell which produces the enzyme. The term "ribozyme" describes an RNA-containing nucleic acid that functions as an enzyme, such as an endoribonuclease, and may be used interchangeably with "enzymatic RNA molecule."

The present invention further includes nucleic acids encoding ribozymes, nucleic acids that encode ribozymes and that have been inserted into an expression vector, host cells containing such vectors, and methodology employing ribozymes to decrease Ss2-ODD1 activity in plants.

In another embodiment, the present invention provides double-stranded nucleic acid molecules of that mediate RNA interference (RNAi) gene silencing. In an embodiment, the siNA molecules of the invention consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In another embodiment, siNA molecules of the invention comprise duplex nucleic acid molecules with overhanging ends of about 1 to about 32 (e.g., about 1, 2, or 3) nucleotides, for example, about 21-nucleotide duplexes with about 19 base pairs and 3'-terminal mononucleotide, dinucleotide, or trinucleotide overhangs. In yet another embodiment, siNA molecules of the invention comprise duplex nucleic acid molecules with blunt ends, where both ends are blunt, or alternatively, where one of the ends is blunt.

A siNA molecule of the present invention may comprise modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

Plants for Genetic Engineering

The present invention comprehends the genetic manipulation of plants to modify plant architecture and enhance biomass and/or sucrose yield.

The term "plant" denotes any cellulose-containing plant material that can be genetically manipulated, including but not limited to differentiated or undifferentiated plant cells, protoplasts, whole plants, plant tissues, or plant organs, or any component of a plant such as a leaf, stem, root, bud, tuber, fruit, rhizome, or the like. The term "propagule" includes a structure with the capacity to give rise to a new plant, e.g., a seed, a spore, or a part of the vegetative body capable of independent growth if detached from the parent.

"Transgenic plant" refers to a plant or progeny thereof derived from a genetically engineered plant cell or protoplast, wherein the plant DNA contains an introduced exogenous DNA molecule. Additionally, the "transgenic plant" category includes a transformant in its lineage, e.g., by way of standard introgression or another breeding procedure, such as conventional breeding. In contrast, a plant that is not genetically manipulated is a control plant and is referred to as a "non-transgenic" plant. Non-transgenic plants can be regenerated from cultured cells or tissues without prior modification by the introduction of a construct comprising polynucleotide sequence. Additionally, "wild-type plant" refers to a non-transgenic plant whose genome is neither modified by the introduction of a construct comprising the polynucleotide sequences or fragment thereof of the present invention nor were regenerated from cultured cells or tissues.

Plants that can be engineered in accordance with the invention include but are not limited to any higher plants, including gymnosperms, monocotyledonous and dicotyledonous plants. The plants of the present invention could include crops, including but not limited to, soybean, wheat, corn, potato, cotton, rice, oilseed rape (including canola), beans, sunflower, alfalfa, sugarcane, turf, barley, rye, millet, sorghum, beet, sugarbeet, cassava, yam, and sweet potato. The plants also may be woody species, such pine, poplar, aspen, willow, and eucalyptus. Also, the plants may be grasses, including but not being limited to *Saccharum, Erianthus, Miscanthus, Narenga, Sclerostachya*, sorghum, maize, teosinte, *Tripsacum*, millets, teff, switchgrass, napiergrass, rice, wild rice, oat, barley, rye, *Brachypodium*, ryegrass, fescue, turf grass, or bamboo species. More specifically, plants that can be engineered in accordance with the invention include but are not limited to woody trees, sugarcane and sorghum.

"Sugarcane plant" is understood as meaning a plant of the genus *Saccharum*, preferably the species *Saccharum officinarum*, and more preferably the interspecific hybrid produced by crossing *Saccharum officinarum* with *Saccharum spontaneum*. "Sorghum" refers to any plant that is a member of the genus *Sorghum*, and includes "sweet sorghum" varieties having high sugar content.

Methods for Genetic Engineering

The polynucleotides of the invention may be used to produce transgenic plants with modified architecture and enhanced plant biomass and/or sucrose yield.

Transgenic plants (including plant cells, plant explants, or plant tissues) incorporating the polynucleotides and/or expressing the polypeptides of the invention can be produced by a variety of well established techniques as described infra and the selection of the most appropriate transformation technique may be determined by the practitioner. Following construction of a vector, most typically an expression cassette, including a polynucleotide, e.g., a Ss2-ODD1 sequence, standard techniques known in the art can be used to introduce and stably integrate the polynucleotide into a plant, a plant cell, a plant explant or a plant tissue of interest. Optionally, the plant cell, explant, or tissue can be regenerated to produce a transgenic plant.

Both monocotyledonous and dicotyledonous angiosperm or gymnosperm plant cells may be transformed. For example, see Klein and Fitzpatrick-McElligott., Current Opinion in *Biotechnology* 4: 583-590, 1993; Bechtold et al., C. R. *Acad. Sci Paris* 316: 1194-1199, 1993; Koncz and Schell, *Mol. Gen.*

Genet. 204: 383-396, 1986; Paszkowski et al., *EMBO J* 3: 2717-2722, 1984; Sagi et al., *Plant Cell Rep.* 13: 262-266, 1994. *Agrobacterium* species such as *A. tumefaciens* and *A. rhizogenes* can be used, for example, in accordance with Nagel et al., *FEMS Microbiol Lett* 67: 325-328, 1990. Additionally, plants may be transformed by *Rhizobium, Sinorhizobium* or *Mesorhizobium* transformation. Broothaerts et al., *Nature* 433: 629-633, 2005.

Additional methods for genetically engineering a plant or cell include but are not limited to electroporation, particle gun bombardment (Klein et al., *Nature* 327: 70-73, 1987), calcium phosphate precipitation, and polyethylene glycol fusion, transfer into germinating pollen grains, direct transformation (Lorz et al., *Mol. Gen. Genet.* 199: 179-82, 1985), and other methods known to the art.

Suitable protocols are available for Poaceae (corn, sugarcane, sorghum, etc.), Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., Handbook of Plant Cell Culture—Crop Species. Macmillan Publ. Co., N.Y., 1984; Shimamoto et al., *Nature* 338: 274-276, 1989; Fromm et al., *Bio/Technology* 8: 833-39, 1990; and Vasil et al., *Bio/Technology* 8: 429-34, 1990. Protocols for sugarcane transformation are of particular interest for the present invention. Sugarcane can be transformed by means of the particle gun bombardment, see Bower & Birch, *Plant Journal* 2: 409-416, 1992; Franks & Birch, *Aust. J. Plant Physiol.* 18: 471-80, 1991; Gallo-Meagher & Irvine, *Crop Science* 36: 1367-1374, 1996; Bower et al., *Molecular Breeding* 2: 239-249, 1996; Snyman et al., *S. Afr. J. Bot.* 62: 151-154, 1996, or by *Agrobacterium*-mediated gene transfer. See, e.g., Arencibia et al., *Transgenic Res.* 7: 213-22, 1998.

Methodology for regenerating a transgenic plant from a transformed cell or culture vary according to the plant species but are based on known methodology. For example, methods for regenerating transgenic sugarcane plants are well-known. See, for instance, Weng et al., *Pest Manag. Sci.* 62: 178-87, 2006; Santosa et al., *Molecular Biotechnology* 28: 113-19, 2004; Bower and Birch, *Plant Journal* 2: 409-416, 1992; and Falco et al., *Plant Cell Reports* 19: 1188-194, 2000.

If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

Transformed plants are selected that have decreased expression of an endogenous 2-ODD1 gene. For example, an inventive transgenic sugarcane plant or cell can be distinguished from wild-type sugarcane by the fact that the transgenic plant or cell comprises at least one copy of the nucleic acid molecule set for in SEQ ID NO: 1 stably integrated into their genome in addition to copies of such a molecule which occur naturally in the sugarcane wild-type plants/plant cells. In this case, the transgenic sugarcane plant/cells, for example, can be distinguished from sugarcane wild-type plants/cells because the additional copy or copies is located at locations in the genome where it does not occur in wild-type plant/cell.

In the context of the present invention, the transgenic plants produced by the methods described supra can be used as a source of a transgene in a conventional breeding program. In general, pollen from a transgenic plant is used to pollinate a non-transgenic plant. The seeds of the mother plant can be used to produce a new transgenic plant different from the original transgenic plant produced by the method described supra.

Methods for Quantifying Enhanced Biomass and Sucrose Yield

Transgenic plants and cells of the invention are characterized by an altered plant architecture and enhanced biomass and/or enhanced sucrose yield. This is achieved by decreasing or suppressing 2-ODD expression.

The term "trait" refers to a physiological, morphological, biochemical, or physical characteristic of a plant or particular plant material or cell. In some instances, this characteristic is visible to the human eye, such as seed or plant size, or can be measured by available biochemical techniques, such as the protein or sucrose content of plant parts or by the observation of the expression level of genes, e.g., by employing Northern analysis, RT-PCR, microarray gene expression assays or reporter gene expression systems, or by agricultural observations such as yield or modified architecture.

In this description, the phrase "enhanced biomass" connotes an increase in biomass in one or more parts of a plant, particularly in aboveground (harvestable) parts, increased root biomass or increased biomass of any other harvestable part, relative to the biomass of the corresponding parts of corresponding non-transgenic plants. "Fiber yield" is understood as meaning the total amount of solid, water insoluble material produced by a plant. For the purposes of this invention, fiber is considered a component of biomass and refers to the bagasse remaining after sugarcane stalks are crushed to extract their juice. "Enhanced fiber yield" refers to an increase in total fiber yield in transgenic plants relative to non-transgenic plants.

"Sucrose yield" is understood as meaning the total amount of sucrose produced by a plant. Sucrose yield is quantified by calculating the total apparent sucrose, which is defined as the product of juice volume that is obtained by crushing the stalk, multiplied by the sucrose concentration in that juice. More preferably, in the context of the present invention, sucrose yield means the total amount of sucrose produced per hectare of a transgenic plantation. The phrase "enhanced sucrose yield" refers to an increase in sucrose content in a transgenic plant in comparison with a non-transgenic one.

"Modified architecture" as defined here includes any change in the appearance or number of any one or more of the leaves, shoots, stems, tillers, inflorescence (for monocotyledonous and dicotyledonous plants), panicles, pollen, ovule, seed, embryo, endosperm, seed coat and aleurone. Additionally or alternatively, "modified architecture" is manifested by at least one of: an increase in plant height and/or weight, an increase in the number of stalk internodes, increase of the stalk internode diameter and/or increase of the stalk internode length, and more homogeneous internode diameter from the bottom to the top of the transgenic plants.

Quantifying Plant Biomass

Enhanced biomass can be determined by measuring more readily discernible characteristics, including but not limited to plant weight and size, stem weight and size, leaf weight and size, root weight and size, and seed number and weight.

A plant having "enhanced biomass" refers to an increase by 2-100%, preferably 5-90%, and more preferably 10-80% of dry and/or fresh weight in a transgenic plant in comparison with a non-transgenic plant.

For the purposes of the present invention, fiber is included in the biomass. In the case of sugarcane, the fiber content usually ranges from 8 to 14% of the fresh weight. As used herein, "fiber" refers to the bagasse or biomass remaining after sugarcane stalks are crushed to extract their juice. Fiber yield is therefore quantified by measuring the bagasse fresh weight with a high capacity precision balance. A sugarcane mill produces nearly 30% of bagasse out of its total crushing. Many research efforts have attempted to use bagasse as a renewable feedstock for power generation and for producing bio-based materials. Additionally, bagasse may be used as a primary fuel source because; when burned in quantity, it produces sufficient heat energy.

A plant having "enhanced the fiber yield" refers to an increase in total fiber yield by 2-70%, preferably by 5-50% and more preferably by 10-40% in comparison with a control plant of the same species or variety.

Quantifying Sucrose Yield

"Sucrose yield" is understood as meaning the total amount of sucrose produced by a plant. Sucrose yield is quantified by calculating the total apparent sucrose, which is defined as the product of juice volume that is obtained by crushing the stalk, multiplied by the sucrose concentration in that juice. More preferably, in the context of the present invention, sucrose yield means the total amount of sucrose produced per hectare of a transgenic sugarcane plantation.

A plant having "enhanced sucrose yield" refers to an increase in total sucrose yield by 2-100%, preferably by 5-90%, and more preferably by 10-80% in comparison with a control plant of the same species or variety.

Evaluating Plant Architecture Modification

In describing a plant of the invention, a plant having "altered plant architecture" refers to an alteration in, for example, plant height, weight, and diameter, tiller number, internode number, length and homogeneity, leaf number, length, width and angle distribution, root length, root length and weight.

The present invention is further described by reference to the following examples, which are illustrative only and not limiting on the invention.

EXAMPLE 1

Identification and Characterization of *Saccharum* spp. 2-oxoglutarate-Dependent dioxygenase (Ss2-ODD1)

Figure 1:
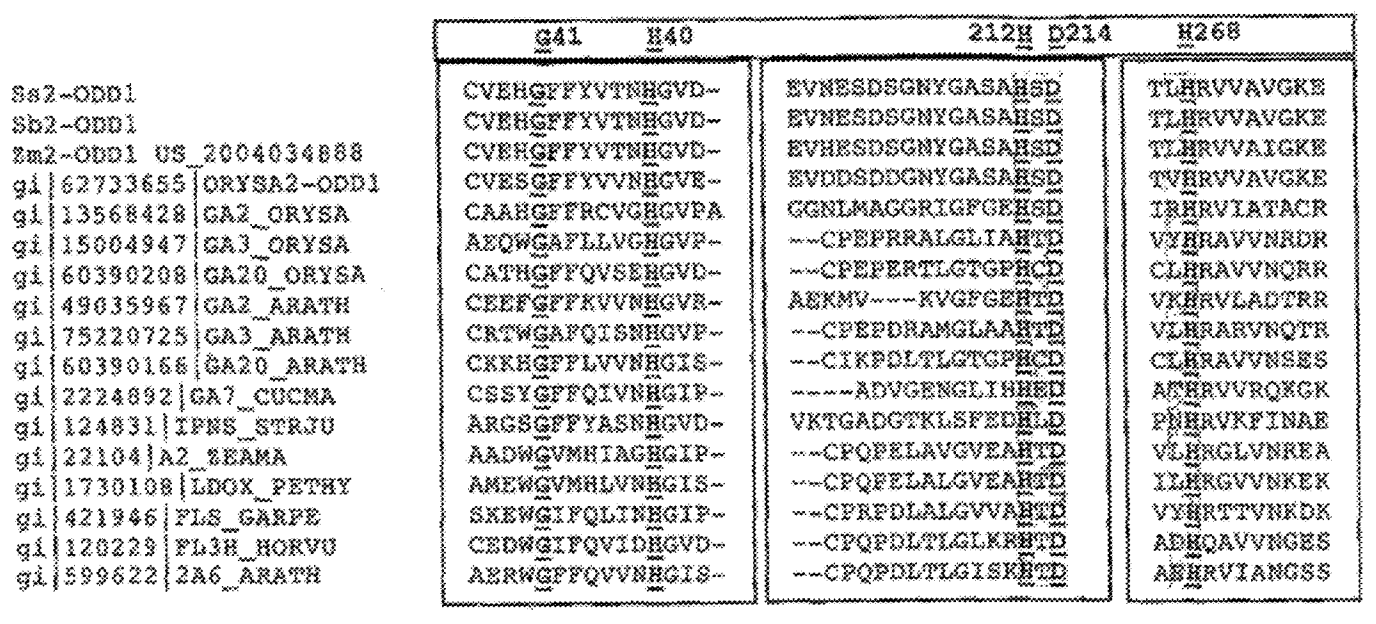

Searches with sequences of 2-ODD homologs from rice were performed in the sugarcane expressed sequence tag (EST) data available at GenBank with the BLAST algorithm. Altschul et al., *J. Mol. Biol.* 215: 403-410, 1990. Searches with a particular rice 2-ODD homolog (gi 27311281) yielded the identification of two clusters encoding a putative 2-ODD homologue. One of these clusters is nearly identical to a 2-ODD cDNA clone incomplete at its 3'-end found at GenBank (gi 35984354). These clusters were found to correspond to a single cDNA clone, named hereafter Ss2-ODD1 (SEQ ID NO: 1). Ss2-ODD1 contains an open reading frame (positions 50 to 982) encoding the probable full-length Ss2-ODD1 polypeptide (SEQ ID NO: 2), as determined by sequence alignment with its most similar plant homologues. Ss2-ODD1 encodes a polypeptide of 310 amino acid residues and calculated molecular mass of 34,452. Searches in the National Center for Biotechnology Information Conserved Domain Database collection revealed a 2-oxoglutarate-dependent dioxygenase domain (pfam03171) present in the carboxy-terminal half (residues 170 through 271) of the Ss2-ODD1 polypeptide. FIG. 1 illustrates the presence of conserved residues in this domain, including the iron binding motif His-X-Asp(53-57)X-His that is common to non-heme Fe(II) dependent dioxygenases (Kreisberg-Zakarin et al., *Antonie Van Leeuwenhoek* 75: 33-39, 1999). These conserved residues are presumed to be necessary for iron binding in the active site (Borovok et al., *Biochemistry* 35: 1981-1987, 1996).

EXAMPLE 2

Phylogenetic Analysis

BLAST searches against the National Center for Biotechnology Information GenBank protein databases with the Ss2-ODD1 sequence yielded some functionally characterized 2-ODD proteins and several 2-ODD-like proteins of unknown function from various higher plant species. Full-length amino acid sequences of members representative of major 2-ODD types were aligned with the Clustal algorithm (Sugawara et al., *Nucleic Acids Res.* 31: 3497-3500, 2003) using the BLOSUM matrix. Phylogenetic analysis was performed by the Neighbor-Joining method (N.J.) using MEGA version 3.1 (Kumar et al., *Brief Bioinform.* 5: 150-163, 2004) with robustness of nodes of the phylogenetic trees assessed by bootstrapping (1,000 resamplings). In the phylogenetic tree thus generated (FIG. 2), major functionally distinct 2-ODD groups are recognizable. Noticeable are a group represented mostly by 1-aminocyclopropane-1-carboxylate oxidases and other group comprising mostly gibberellic acid-2, -3, and -20 oxidases. In the latter are proteins encoded by genes that affect gibberellin metabolism in *Arabidopsis thaliana* and *Oryza sativa* and *Pisum sativum*. Ss2-ODD1 belongs to a distinct group of functionally non-characterized 2-ODDs, along with several homologs from *Arabidopsis thaliana, Catharanthus roseus, Medicago truncatula, Oryza sativa, Sorghum bicolor*, and *Zea mays*. The identification of Ss2-ODD1-related sequences across this range of species suggests broad conservation of this group in the monocotyledoneous and dicotyledoneous clades.

EXAMPLE 3

Vector Construction

A 619 bp fragment, which spans the nucleotides 58 to 676 of the Ss2-ODD1 cDNA (SEQ ID NO: 1), was obtained by RT-PCR using total RNA isolated from immature leaves of the *Saccharum* hybrid cultivar SP80 1842. Oligonucleotides Ss2-ODD1as Fwd (SEQ ID NO: 3, CGC GGATCCGAACCTGCACCTCCCCGT) and Ss2-ODD1as Rev (SEQ ID NO: 4, CGG ACTAGTCAGGCCAGGAGTGCCATC) were designed based on the sequence of an Ss2-ODD1 EST (GenBank gi 35984354). BamHI and SpeI sites (underlined) were designed into primers Ss2-ODD1as Fwd and Ss2-ODD1as Rev, respectively. The amplified fragment was cloned into pGEM-T Easy (Promega), verified by sequencing, and excised by digestion with SpeI and BamHI. Digestion products were separated by agarose-gel electrophoresis, purified, and cloned at the AvrII and BamHI sites of pUBI (Christensen and Quail, *Transgenic Res.* 5: 213-218, 1996), placing the Ss2-ODD1 fragment, in antisense orientation, between the polyubiquitin gene UBI-1 promoter from maize and the nopaline synthase gene NOS transcriptional terminator from *Agrobacterium tumefaciens*. The resulting construct was verified by sequencing. This construct was digested with HindIII to release the UBI-1::Ss2-ODD1as::NOS cassete. (FIG. 3). The cassete UBI-1::Bar::NOS (Christensen and Quail, *Transgenic Res.* 5: 213-218, 1996) cloned in pBLUE-SCRIPT SK– was released by digestion with EarI (FIG. 3).

Digestion products were separated by agarose-gel electrophoresis, and the fragments corresponding to UBI-1::Ss2-ODD1as::NOS and UBI-1::Bar::NOS cassettes were purified and used for embryogenic sugarcane calli transformation.

EXAMPLE 4

Sugarcane Transformation

Embryogenic calli cultures were established from apical meristems and primordial leaves of *Saccharum* hybrid cultivar RB835486. Eight-week old calli were transformed by particle bombardment as described previously (Klein et al., *Plant Physiol.* 91: 440-444, 1989) with equimolar concentrations of UBI-1::Bar::NOS and UBI-1::Ss2-ODD1as::NOS expression cassettes (10 µg DNA/3 mg particle). After bombardment, calli were transferred to MS medium (Murashige and Skoog, *Physiol Plant* 15: 473-479, 1962) containing 1 mg/L phosphinothricin (PPT) and 1 mg/L benzylaminopurine (BAP) to inhibit development of non transgenic tissue and promote shoot regeneration. Two weeks later, calli were transferred to MS medium containing 1 mg/L PPT and 1 mg/L indole-3-butyric acid (IAB) for shoot elongation and to induce root formation. After two weeks, plantlets were placed into magenta boxes for acclimatization, and 2 weeks later shoots (10-15 cm tall) with well-developed roots were transferred to potting soil and placed in a greenhouse. The regenerated transgenic plants were genotyped by PCR analysis for the presence of the selectable marker gene (Bar) and the UBI::Ss2-ODD1as::NOS transgene. Tissue-cultured, non-transgenic controls were obtained by regenerating plants from embryogenic calli of the *Saccharum* hybrid cultivar RB835486 as described above, except for omitting particle bombardment with expression cassettes and phosphinothricin selection. Plants were propagated via stem cuttings.

EXAMPLE 5

Alteration of Plant Architecture in UBI-1::Ss2-ODD1as::NOS Plants

To assess the effect of reducing Ss2-ODD1 expression in transgenic sugarcane plants, UBI-1::Ss2-ODD1as::NOS independent transgenic events and non-transgenic wild type plants of the sugarcane variety RB835486 were evaluated in a greenhouse. Plants (12 replicates per event) were grown in coconut shell fiber substrate in 50-L pots. Plants were irrigated three times per day (totaling 1.5 L) with a nutrient solution. Up to four tillers per plant were allowed to develop, and the exceeding ones were manually removed. Seven months after seedling emergence, the irrigation regime was switched to three cycles of irrigation per day with tap water (totaling 250 mL) for 14 days to induce maturation. The two most homogeneous tillers from each replicate were selected for analyses, and their stalks were sectioned below their oldest node. The eight internodes below the first visible dewlap were identified, the stalks were sectioned at the nodes between the seventh and eighth internodes, and the apical section of the stalks was discarded along with all leaves. Stalk height and weight, and internode number, width, and length were measured. Analysis of variance (ANOVA) and Dunnett's test for mean comparison for all measurements were performed with MINITAB Release 14.

During the stages of plant growth prior to their complete characterization, various UBI-1::Ss2-ODD1as::NOS events showed perceptible alterations in their dimensions compared to the non-transgenic control cultivar RB835486. Measurements at seven months after seedling emergence revealed that events 06, 09, 12, 13, 14, 15, 18, and 21 had significantly increased height (FIG. 4) compared to the non-transgenic control. In events 09, 13, 14, and 15, this is likely due to a significantly increased internode number (FIG. 5), while in events 12, 18, and 21 this is likely a consequence of a significantly increased mean internode length (FIG. 6). Measurements also revealed that internode diameter is significantly increased in events 06 and 21 (FIG. 7). As a result of their increased overall dimension, events 06, 09 and 21 had significantly enhanced biomass, as illustrated by their stalk fresh weight (FIG. 8). Altogether, reduction of Ss2-ODD1 expression appears to cause, at various degrees, changes in plant architecture that lead to increased dimension.

EXAMPLE 6

Enhanced Sucrose Yield in UBI-1::Ss2-ODD1as::NOS Plants

To assess the effect of reducing Ss2-ODD1 expression in transgenic sugarcane plants, UBI-1::Ss2-ODD1as::NOS independent transgenic events and non-transgenic wild type plants of the sugarcane variety RB835486 were evaluated in a greenhouse. Plants (12 replicates per event) were grown in coconut shell fiber substrate in 50-L pots. Plants were irrigated three times per day (totaling 1.5 L) with a nutrient solution. Up to four tillers per plant were allowed to develop, and the exceeding ones were manually removed. Seven months after seedling emergence, the irrigation regime was switched to three cycles of irrigation per day with tap water (totaling 250 mL) for 14 days to induce maturation. The two most homogeneous tillers from each replicate were selected for analyses, and their stalks were sectioned below their oldest node. The eight internodes below the first visible dewlap were identified, the stalks were sectioned at the nodes between the seventh and eighth internodes, and the apical section of the stalks was discarded along with all leaves. For the assessment of appropriate maturation induction, total soluble solids were measured with a handheld Reichert Brix Scale Refractometer and the ratio between the values obtained for the eight and antepenultimate internodes were calculated. The ratio was found to be larger than 80% in all cases, which is a positive indication of maturation. A three-roller power crusher was used to extract the juice from the stalks. The juice was immediately filtered through a stainless steel sieve. Volume of juice was measured, which was again filtered through a 120-mesh sieve. Estimation of total soluble solids and sucrose concentration in the juice was immediately performed. Juice total soluble solids were measured by refractometry with a Bellingham+Stanley RFM840 Digital Refractometer. Following clarification with a mixture of calcium hydroxide, aluminum chloride hexahydrate and Celite, juice sucrose concentration was estimated by measuring the circular birefringence with a Zeiss Polomat A polarimeter. Sucrose concentration in the juice was expressed as % POL, which indicates the number of grams of sucrose per 100 mL of solution. Total apparent sucrose was calculated as a product of juice volume multiplied by sucrose concentration in it (POL). Analysis of variance (ANOVA) and Dunnett's test for mean comparison were performed with MINITAB Release 14.

Events 06 and 09 had significantly increased juice volume compared to the non-transgenic control cultivar RB835486 (FIG. 9), while events 13, 14, and 21 had significantly increased sucrose concentration in the juice (FIG. 10). As an estimate for sucrose yields, we calculated the total apparent sucrose. This analysis revealed that events 09, 13, 14, 20, and 21 had significantly increased sucrose yield (FIG. 11). Thus, reduction of Ss2-ODD1 expression appears to cause changes in juice volume and its sucrose concentration that lead to an increased sucrose yield.

EXAMPLE 7

Enhanced Biomass Yield in UBI-1::Ss2-ODD1as::NOS Plants

To assess the effect of reducing Ss2-ODD1 expression in transgenic sugarcane plants, UBI-1:: Ss2-ODD1 as::NOS independent transgenic events and non-transgenic wild type plants of the sugarcane variety RB835486 were evaluated in a greenhouse. Plants (12 replicates per event) were grown in coconut shell fiber substrate in 50-L pots. Plants were irrigated three times per day (totaling 1.5 L) with a nutrient solution. Up to four tillers per plant were allowed to develop, and the exceeding ones were manually removed. Seven months after seedling emergence, the irrigation regime was switched to three cycles of irrigation per day with tap water (totaling 250 mL) for 14 days to induce maturation. The two most homogeneous tillers from each replicate were selected for analyses, and their stalks were sectioned below their oldest node. The eight internodes below the first visible dewlap were identified, the stalks were sectioned at the nodes between the seventh and eighth internodes, and the apical section of the stalks was discarded along with all leaves. A three-roller power crusher was used to extract the juice from the stalks. Following stalk crushing for juice extraction, the bagasse fresh weight was measured with a high capacity precision balance. Analysis of variance (ANOVA) and Dunnett's test for mean comparison were performed with MINITAB Release 14.

This analysis revealed that events 9 and 21 had significantly increased amounts of bagasse fresh weight compared to the non-transgenic control (FIG. 12), indicating that these events have increased biomass yield.

EXAMPLE 8

Expression of Ss2-ODD1 Transcripts in Sugarcane Organs

To determine the spatial and temporal abundance of Ss2-ODD1 transcripts, we performed quantitative reverse transcription-polymerase chain reaction (qRT-PCR) using RNA isolated from different organs of wild-type sugarcane plants (cultivar RB835486). Blade of the youngest leaf, shoot apex, blade of leaf +4, sheath of leaf +4, internode +4, blade of the oldest green leaf, sheath of the oldest green leaf, internode connected to the oldest green leaf, antepenultimate internode (from apex to base), and roots were harvested from 8-month old, greenhouse grown plants. Leaf +4 is defined as the fourth youngest leaf with a clearly visible dewlap at the blade joint. Whole leaves and roots were harvested from 30-cm tall seedlings of the same cultivar. Three independent 8 month-old plants and three pools comprising three seedlings each were used in this analysis. Liquid $N_2$-frozen tissue was ground to powder with mortar and pestle, and total RNA was isolated with the Trizol reagent (Invitrogen) according to the manufacturer's instruction. Total RNA was treated with DNaseI (Promega), and cDNA first strand was synthesized with SuperScript II Reverse Transcriptase (Invitrogen) using 2 μg of total RNA. One tenth of the cDNA was used in combination with gene specific primers at 500 nM concentration and SYBR Green PCR Master Mix (Applied Biosystems). PCR was performed on an ABI Prism 7000 Sequence Detection System (Applied Biosystems). For amplification of Ss2-ODD1 transcripts, oligonucleotide primers Ss2-ODD1 Fwd (SEQ ID NO: 5, CAGTTGGTAAAGAGCGGTATTCG-GTGGC) and Ss2-ODD1 Rev (SEQ ID NO: 6, CTTGATAG-GTGGAAACCTTGGTGGACATGC), which anneal at the 3' end of Ss2-ODD coding sequence (base pair 770 to 880) were used. Actin (SsACT; GenBank gi 53759188), used as a reference gene, was amplified with oligonucleotide primers SsACT Fwd (SEQ ID NO: 7, AAGCAGCATGAAGAT-CAAGGTCGTTGCAC) and SsACT Rev (SEQ ID NO: 8, CTGTGAACAATTGCCGGGCCAGACTC), which anneal at the 3' end of SsACT coding sequence (base pair 972 to 1121). Amplification was performed at 50° C. for 2 min, 95° C. for 10 min, and 45 cycles at 95° C. for 15 sec and 60° C. for 1 min. The specificity of the amplification reaction was evaluated by the analysis of the dissociation curves. The ratio between the amounts of the Ss2-ODD1 and SsACT amplified products was calculated using the $2^{-\Delta\Delta Ct}$ method (Livak and Schmittgen, Methods 25: 402-408, 2001). The normalized expression level for each replicate was calculated as $L=2^{-\Delta Ct}$ and $\Delta CT=CT,Ss2-ODD1-CT,SsACT$. Ss2-ODD1 transcript levels relative to those of SsACT were calculated as the average of values obtained from three independent samples used as biological replicates for each organ. Results from this analysis are shown in FIG. 13.

Ss2-ODD1 transcripts were detected in all organs analyzed and, in agreement with its low frequency in ESTs libraries, appeared to be much less abundant than SsACT transcripts, suggesting a low expression level. Ss2-ODD1 transcripts were most abundant in leaf blades of 8 month-old plants. The highest expression level was found in the blade of the oldest green leaf, followed by blades of leaf +4 and youngest leaf. Seedling whole leaf showed an intermediate expression level. Lower transcript levels were found in leaf sheath, root, internode, and shoot apex of 8 month-old plants, and the expression was the lowest in seedling root. Although the overall expression pattern indicates that Ss2-ODD1 shows a rather ubiquitous expression, it suggests a function for Ss2-ODD1 in actively photosynthesizing leaves.

EXAMPLE 9

Purification of Ss2-ODD1 Recombinant Protein and Generation of polyclonal Ss2-ODD1

Expression of the UBI-1::Ss2-ODD1as::NOS transgene-derived antisense transcripts were aimed at decreasing Ss2-ODD1 protein abundance. We sought to produce polyclonal antibodies against recombinant Ss2-ODD1 protein for its immunodetection in UBI-1::Ss2-ODD1as::NOS events and non-transgenic controls to verify whether transgene-derived antisense transcripts decreased Ss2-ODD1 protein abundance.

The full-length Ss2-ODD1 coding sequence was amplified from cDNA prepared from sugarcane (Saccharum hybrid cultivar RB835486) leaves with HiFi Taq DNA polymerase (Invitrogen) with the Ss2-ODD1 CDS primer (SEQ ID NO: 9, AGCATGGCAGGCAACCTGCACCTCCCCGTG) and the Ss2-ODD1 CDS primer (SEQ ID NO: 10, CTTATTTGTAT-GTCGAATTTATTCGCCCAACTACGTATTCCCCAC). The resulting 936-bp amplified fragment was cloned into pET SUMO (Invitrogen) according to the manufacturer's instructions, and its nucleotide sequence was verified by sequencing. The resulting construct, pET SUMO-Ss2-ODD1, encodes a fusion protein consisting of a hexahistidine-tagged (SEQ ID NO: 62), small ubiquitin modifier (SUMO) polypeptide fused at the amino terminus of Ss2-ODD1 (SUMO-Ss2-ODD1). A serine codon was added, prior the Ss2-ODD1 translation start methionine codon, via the forward oligonucleotide primer to facilitate the removal of SUMO by digestion with SUMO protease (Invitrogen). pET SUMO-Ss2-ODD1 was transformed into *Escherichia coli* CY(DE3) pLysS strain (Farah and Reinach, *Biochemistry* 38: 10543-10551, 1999) and expression of SUMO-Ss2-ODD1 fusion protein was attained by induction of cell cultures at O.D.$_{600}$~0.5 with 1 mM isopropyl-β-D-thiogalactopyranoside at 37° C. for 3 hr. Cells were collected by centrifugation and lysed in PBS pH 7.2 supplemented with 0.2 mg/mL lysozyme for 30 mM on ice, followed by sonication. Lysates were cleared by centrifugation at 15,000 g for 15 min. Ten mM imidazole was added to the supernatant and the SUMO-Ss2-ODD1 fusion protein was bound to Ni$^{+2}$ on a 1-mL HiTrap HP column (Amersham). After extensive washing with 10 mM imidazole on phosphate buffer saline (PBS) pH 7.2, the SUMO-Ss2-ODD1 fusion protein was eluted with a 10-500 mM imidazole gradient on PBS pH 7.2. Native Ss2-ODD1 protein was obtained by cleavage of affinity-purified SUMO-Ss2-ODD1 with SUMO protease (Invitrogen) and further purified following the manufacturer's instructions, except for carrying out the digestion by SUMO protease at 25° C. for 4 h.

Native Ss2-ODD1 (150 μg) was injected in rabbits with Freund's complete adjuvant. Three boost injections were made with 150 μg of Ss2-ODD1 and Freund's incomplete adjuvant. Antibodies were affinity-purified from crude sera as described by Harlow and Lane (ANTIBODIES: A LABORATORY MANUAL, Cold Spring Harbor Laboratory Press, Cold Spring Harbor, N.Y., 1988). An IgG-enriched fraction was obtained from crude antisera by precipitation at 50% ammonium sulfate saturation. The resulting pellet was solubilized in PBS pH 7.2, and dialyzed. This fraction was depleted of non-Ss2-ODD1 antibodies by continuous circulation on a 1-mL HiTrap HP column (Amersham) with bound hexahistidine-tagged (SEQ ID NO: 62) SUMO-CAT (chloramphenicol acetyl transferase) fusion protein expressed from the construct pET SUMO-CAT (Invitrogen) overnight at 4° C. Subsequently, the flowthrough fraction was continuously circulated on a 1-mL HiTrap NHS-activated HP column (GE Healthcare Bio-Sciences AB) with covalently linked SUMO-Ss2-ODD1 fusion protein overnight at 4° C. The antibody-adsorbed column was washed extensively with PBS pH 7.2, and antibodies were eluted with 100 mM NaCl, 100 mM glycine, pH 2.4. Collected fractions were immediately neutralized with 0.1 volumes of 2 M Tris-HCl pH 8.0; those containing the bulk of IgG were pooled and concentrated with Centricon-10 spin cartridges (Millipore), followed by extensive buffer exchange with PBS pH 7.2.

EXAMPLE 10

Ss2-ODD1 Protein Levels in
UBI-1::Ss2-ODD1as::NOS Events and
Non-Transgenic Controls Using affinity-purified polyclonal antibodies raised against recombinant, native Ss2-ODD1, we performed immunoblot analysis of Ss2-ODD1 in organs of UBI-1::Ss2-ODD1as::NOS events and non-transgenic control plants to verify whether transgene-derived antisense transcripts decreased Ss2-ODD1 protein abundance. For each transgenic event or wild-type control, blades of leaf +4 were harvested from 8-month old, greenhouse grown plants. Leaf +4 is defined as the fourth youngest leaf with a clearly visible dewlap at the blade joint.

Harvested plant material was immediately frozen in liquid N$_2$, stored at −80° C. for subsequent processing, was homogenized into a fine powder in liquid N$_2$, and transferred to conical microcentrifuge tubes. Three volumes of ice-cold extraction buffer (100 mM Tris-HCl pH 6.8, 5 mM EDTA, 0.1% SDS, 175 mM β-mercaptoethanol, 10% glycerol) supplemented with Complete EDTA-free Protease Inhibitor Cocktail (Roche Diagnostics GmbH) was added to the ground tissue and kept under constant agitation for 20 min at 4° C. Homogenates were cleared by centrifugation at 15,000 g for 15 mM at 4° C. Protein concentration was determined by the Bradford assay (Protein Assay kit, Bio-Rad), using BSA as standard. Soluble protein extracts (50 μg) were separated by 12.5% SDS-PAGE, and blotted onto polyvinylidene difluoride membranes (Hybond-P PVDF, Amersham) in a tank transfer system (Mini Trans-Blot Cell, Bio-Rad) at 150 Volts X hours in TGM buffer (25 mM Tris, 192 mM glycine, 20% methanol). Membranes were blocked with 9% fat-free milk solids in TBST (20 mM Tris-HCl pH 7.5, 150 mM NaCl, 0.05% Tween-20), and incubated with affinity-purified antibodies at 1:1,000 dilution in TBST overnight at RT. Membranes were washed with TBST for 10 min three times and incubated with a 1:10,000 dilution of a donkey anti-rabbit IgG conjugated to horseradish peroxidase (GE Healthcare Bio-Sciences AB) in TBST for 1.5 h at RT. Membranes were subsequently washed three times with TBST, and developed with ECL Plus (GE Healthcare Bio-Sciences AB) followed by exposure to radiographic film (Hyperfilm ECL; GE Healthcare Bio-Sciences AB) for various time intervals.

Utilizing affinity-purified antibodies, Ss2-ODD1 was detected as a polypeptide of approximately 34 kD in extracts prepared from blades of leaf +4, corresponding in size to recombinant, native Ss2-ODD1 protein (FIG. 14). Blades of leaf +4 from events 9, 14 and 21 had, at different degrees, decreased amounts of Ss2-ODD1 protein compared to wild-type control (FIG. 14). Differences observed ranged from partial reduction to nearly complete abolishment of Ss2-ODD1 protein expression. Ss2-ODD1 protein was hardly detected in event 14, indicating that expression of Ss2-ODD1 antisense transcripts caused a drastic reduction in Ss2-ODD1 protein expression. Events 9 and 21 had Ss2-ODD1 protein levels intermediate to those observed in event 14 and wild-type control. Event 9 apparently had the least reduction of Ss2-ODD1 protein levels among the events analyzed.

Reduction in Ss2-ODD1 protein levels in blades of leaf +4 were not highly correlated with the manifested phenotypes observed in the UBI-1::Ss2-ODD1as::NOS analyzed. Besides being event-dependent, possibly the extent of reduction in Ss2-ODD1protein levels varies in different organs, and phenotypes are best correlated with changes in Ss2-ODD1 abundance in organs other than blades of leaf +4. Also, it is possible that changes in Ss2-ODD1 protein levels must be optimally regulated so that most favorable phenotypic effects are attained.

What is claimed is:

1. A transgenic plant comprising a nucleic acid construct that downregulates expression of an endogenous Ss2-ODD1 functional homolog DNA sequence of the transgenic plant by antisense suppression, sense co-suppression, RNA interference, or enzymatic RNA targeted to said Ss2-ODD1 functional homolog such that the expression of said Ss2-ODD1 functional homolog DNA sequence is reduced compared to a wild-type control plant thereby resulting in the transgenic plant having increased sucrose yield or increased biomass compared to said wild-type control plant, and wherein said transgenic plant is selected from the group consisting of the following:
   (a) sorghum, wherein said endogenous Ss2-ODD1 functional homolog DNA sequence encodes a 2-oxoglutarate-dependent dioxygenase protein comprising SEQ ID NO:14, SEQ ID NO:15 and SEQ ID NO:16, and said 2-oxoglutarate-dependent dioxygenase protein is Sb2-ODD1 shown in FIG. 2;
   (b) corn, wherein said endogenous Ss2-ODD1 functional homolog DNA sequence encodes a protein comprising SEQ ID NO:63; and
   (c) rice, wherein said endogenous Ss2-ODD1 functional homolog DNA sequence encodes a protein comprising SEQ ID NO:64.

2. A method for producing sucrose, said method comprising obtaining sucrose from a transgenic plant having a nucleic acid construct that suppresses expression of an endogenous Ss2-ODD1 functional homolog protein by antisense suppression, sense co-suppression, RNA interference, or enzymatic RNA targeted to said Ss2-ODD1 functional homolog in said transgenic plant compared to a wild-type control plant that does not contain the nucleic acid construct thereby resulting in said transgenic plant having increased sucrose yield compared to said wild-type control plant, wherein said transgenic plant is selected from the group consisting of the following:
   (a) sorghum, wherein said endogenous Ss2-ODD1 functional homolog DNA sequence encodes a 2-oxoglutarate-dependent dioxygenase protein comprising SEQ ID NO:14, SEQ ID NO:15 and SEQ ID NO:16, and said 2-oxoglutarate-dependent dioxygenase protein is Sb2-ODD1 shown in FIG. 2;
   (b) corn, wherein said endogenous Ss2-ODD1 functional homolog DNA sequence encodes a protein comprising SEQ ID NO:63; and
   (c) rice, wherein said endogenous Ss2-ODD1 functional homolog DNA sequence encodes a protein comprising SEQ ID NO:64.

3. A method for producing biomass, said method comprising obtaining biomass from a transgenic plant having a nucleic acid construct that suppresses expression of an endogenous Ss2-ODD1 functional homolog protein by antisense suppression, sense co-suppression, RNA interference, or enzymatic RNA targeted to said Ss2-ODD1 functional homolog in said transgenic plant compared to a wild-type control plant that does not contain the nucleic acid construct thereby resulting in said transgenic plant having increased biomass compared to said wild-type control plant, wherein said transgenic plant is selected from the group consisting of the following:

(a) sorghum, wherein said endogenous Ss2-ODD1 functional homolog DNA sequence encodes a 2-oxoglutarate-dependent dioxygenase protein comprising SEQ ID NO:14, SEQ ID NO:15 and SEQ ID NO:16, and said 2-oxoglutarate-dependent dioxygenase protein is Sb2-ODD1 shown in FIG. 2;

(b) corn, wherein said endogenous Ss2-ODD1 functional homolog DNA sequence encodes a protein comprising SEQ ID NO:63; and (c) rice, wherein said endogenous Ss2-ODD1 functional homolog DNA sequence encodes a protein comprising SEQ ID NO:64.

4. A method for enhancing sucrose yield in a plant, said method comprising suppressing expression of an endogenous Ss2-ODD1 functional homolog protein by antisense suppression, sense co-suppression, RNA interference, or enzymatic RNA targeted to said Ss2-ODD1 functional homolog in said plant thereby resulting in said a transgenic plant having increased sucrose yield compared to a wild-type control plant, wherein said transgenic plant is selected from the group consisting of the following:

(a) sorghum, wherein said endogenous Ss2-ODD1 functional homolog DNA sequence encodes a 2-oxoglutarate-dependent dioxygenase protein comprising SEQ ID NO:14, SEQ ID NO:15 and SEQ ID NO:16, and said 2-oxoglutarate-dependent dioxygenase protein is Sb2-ODD1 shown in FIG. 2;

(b) corn, wherein said endogenous Ss2-ODD1 functional homolog DNA sequence encodes a protein comprising SEQ ID NO:63; and (c) rice, wherein said endogenous Ss2-ODD1 functional homolog DNA sequence encodes a protein comprising SEQ ID NO:64.

* * * * *

SEQUENCE LISTING

```
<160> NUMBER OF SEQ ID NOS: 64

<210> SEQ ID NO 1
<211> LENGTH: 1119
<212> TYPE: DNA
<213> ORGANISM: Saccharum sp.
<220> FEATURE:
<221> NAME/KEY: CDS
```

<222> LOCATION: (50)..(982)

<400> SEQUENCE: 1

| | | |
|---|---|---|
| ccacgcgtcc gctgctccag ccaagccgga gacgtcagag acatcggag atg gca ggg<br>                                                                          Met Ala Gly<br>                                                                          1 | | 58 |
| aac ctg cac ctc ccc gtg gtg gac ctg gcg tcg ccg gac ctc cgc gcc<br>Asn Leu His Leu Pro Val Val Asp Leu Ala Ser Pro Asp Leu Arg Ala<br> 5                         10                      15 | | 106 |
| gcc gct gaa tcc gtc cga cag gcg tgc gtg gag cac ggg ttc ttc tac<br>Ala Ala Glu Ser Val Arg Gln Ala Cys Val Glu His Gly Phe Phe Tyr<br>20                     25                    30                  35 | | 154 |
| gtg acc aac cac gga gtg gac cgc ggc ctg ctc gag gcg gtg ttc gcg<br>Val Thr Asn His Gly Val Asp Arg Gly Leu Leu Glu Ala Val Phe Ala<br>               40                    45                    50 | | 202 |
| cag agc aag ggg ttc ttc gac ctg ccg atg gag gag aag atg gcg ctg<br>Gln Ser Lys Gly Phe Phe Asp Leu Pro Met Glu Glu Lys Met Ala Leu<br>55                     60                    65 | | 250 |
| ctg agg agc gcc aac cac cgc ggg tac acg ccg ccc tac gcc gag aag<br>Leu Arg Ser Ala Asn His Arg Gly Tyr Thr Pro Pro Tyr Ala Glu Lys<br>        70                    75                    80 | | 298 |
| ctc gac gcc tct tcc cag ttc gta gga gac ctc aag gag agt ttc tac<br>Leu Asp Ala Ser Ser Gln Phe Val Gly Asp Leu Lys Glu Ser Phe Tyr<br>85                     90                    95 | | 346 |
| att ggg cct att gat gat ggc gat atg cat aac gat ata aac caa tgg<br>Ile Gly Pro Ile Asp Asp Gly Asp Met His Asn Asp Ile Asn Gln Trp<br>100                   105                 110               115 | | 394 |
| cct tct gaa gag cgc ttg cca tct tgg aag gag aca atg aag cta tac<br>Pro Ser Glu Glu Arg Leu Pro Ser Trp Lys Glu Thr Met Lys Leu Tyr<br>               120                   125                 130 | | 442 |
| att gca gct gtt ctg gat act ggc aca agg ata ctc tct cta att gct<br>Ile Ala Ala Val Leu Asp Thr Gly Thr Arg Ile Leu Ser Leu Ile Ala<br>                     135                   140                 145 | | 490 |
| ttg ggt ttg gat ttg gat gct gat ttc ttt cat aaa att ggt gca ttg<br>Leu Gly Leu Asp Leu Asp Ala Asp Phe Phe His Lys Ile Gly Ala Leu<br>150                   155                 160 | | 538 |
| aac tgc ccg tcg aca ttt ctt cgg tta ttg cat tac cca ggt gaa gta<br>Asn Cys Pro Ser Thr Phe Leu Arg Leu Leu His Tyr Pro Gly Glu Val<br>        165                    170                 175 | | 586 |
| aat gag tct gat agt gga aac tac ggt gca tca gct cac tcg gac tat<br>Asn Glu Ser Asp Ser Gly Asn Tyr Gly Ala Ser Ala His Ser Asp Tyr<br>180                   185                 190               195 | | 634 |
| ggt gtg ata acc ctt tta gtg aca gat ggc act cct ggc ctg cag ata<br>Gly Val Ile Thr Leu Leu Val Thr Asp Gly Thr Pro Gly Leu Gln Ile<br>               200                   205                 210 | | 682 |
| tgc agg gag aag gat agg aat ccc cag cta tgg gaa gat gtt cat cac<br>Cys Arg Glu Lys Asp Arg Asn Pro Gln Leu Trp Glu Asp Val His His<br>                     215                   220                225 | | 730 |
| gtt gat ggg gcc ctt att att aat att ggt gat tgc cta gag agg tgg<br>Val Asp Gly Ala Leu Ile Ile Asn Ile Gly Asp Leu Leu Glu Arg Trp<br>230                   235                 240 | | 778 |
| acg aat tgt gtt ttc aga tct acg ttg cat cgt gtt gtt gca gtt ggt<br>Thr Asn Cys Val Phe Arg Ser Thr Leu His Arg Val Val Ala Val Gly<br>        245                    250                 255 | | 826 |
| aaa gag cgg tat tcg gtg gct ttc ttt ctt gat cca aat cct gac aca<br>Lys Glu Arg Tyr Ser Val Ala Phe Phe Leu Asp Pro Asn Pro Asp Thr<br>260                   265                 270               275 | | 874 |
| ctg gtg cag tgt ttg gaa agt tgt tgc agt gaa gca tgt cca cca agg<br>Leu Val Gln Cys Leu Glu Ser Cys Cys Ser Glu Ala Cys Pro Pro Arg<br>               280                   285                 290 | | 922 |

```
ttt cca cct atc aag agt ggg gaa tac gta gtt ggg cga ata aat tcg      970
Phe Pro Pro Ile Lys Ser Gly Glu Tyr Val Val Gly Arg Ile Asn Ser
            295                 300                 305 aca tac aaa taa tcatccatca catttgtaat gctatgctcc tttataacag         1022
Thr Tyr Lys
        310 cttgatacca taataatgtt tgaacccagg attaaagtta ttttttcatt aacgggcaac   1082 gaaccctgat cgcttgaact taaaaaaaaa aaaaaag                            1119

<210> SEQ ID NO 2
<211> LENGTH: 310
<212> TYPE: PRT
<213> ORGANISM: Saccharum sp.

<400> SEQUENCE: 2

Met Ala Gly Asn Leu His Leu Pro Val Val Asp Leu Ala Ser Pro Asp
1               5                   10                  15

Leu Arg Ala Ala Glu Ser Val Arg Gln Ala Cys Val Glu His Gly
            20                  25                  30

Phe Phe Tyr Val Thr Asn His Gly Val Asp Arg Gly Leu Leu Glu Ala
            35                  40                  45

Val Phe Ala Gln Ser Lys Gly Phe Phe Asp Leu Pro Met Glu Glu Lys
    50                  55                  60

Met Ala Leu Leu Arg Ser Ala Asn His Arg Gly Tyr Thr Pro Pro Tyr
65                  70                  75                  80

Ala Glu Lys Leu Asp Ala Ser Ser Gln Phe Val Gly Asp Leu Lys Glu
                85                  90                  95

Ser Phe Tyr Ile Gly Pro Ile Asp Asp Gly Asp Met His Asn Asp Ile
            100                 105                 110

Asn Gln Trp Pro Ser Glu Glu Arg Leu Pro Ser Trp Lys Glu Thr Met
        115                 120                 125

Lys Leu Tyr Ile Ala Ala Val Leu Asp Thr Gly Thr Arg Ile Leu Ser
    130                 135                 140

Leu Ile Ala Leu Gly Leu Asp Leu Asp Ala Asp Phe Phe His Lys Ile
145                 150                 155                 160

Gly Ala Leu Asn Cys Pro Ser Thr Phe Leu Arg Leu Leu His Tyr Pro
                165                 170                 175

Gly Glu Val Asn Glu Ser Asp Ser Gly Asn Tyr Gly Ala Ser Ala His
            180                 185                 190

Ser Asp Tyr Gly Val Ile Thr Leu Leu Val Thr Asp Gly Thr Pro Gly
        195                 200                 205

Leu Gln Ile Cys Arg Glu Lys Asp Arg Asn Pro Gln Leu Trp Glu Asp
    210                 215                 220

Val His His Val Asp Gly Ala Leu Ile Ile Asn Ile Gly Asp Leu Leu
225                 230                 235                 240

Glu Arg Trp Thr Asn Cys Val Phe Arg Ser Thr Leu His Arg Val Val
                245                 250                 255

Ala Val Gly Lys Glu Arg Tyr Ser Val Ala Phe Phe Leu Asp Pro Asn
            260                 265                 270

Pro Asp Thr Leu Val Gln Cys Leu Glu Ser Cys Cys Ser Glu Ala Cys
        275                 280                 285

Pro Pro Arg Phe Pro Pro Ile Lys Ser Gly Glu Tyr Val Val Gly Arg
    290                 295                 300

Ile Asn Ser Thr Tyr Lys
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcggatccg aacctgcacc tccccgt                                         27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggactagtc aggccaggag tgccatc                                         27

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagttggtaa agagcggtat tcggtggc                                        28

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttgataggt ggaaaccttg gtggacatgc                                      30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagcagcatg aagatcaagg tcgttgcac                                       29

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgtgaacaa ttgccgggcc agactc                                          26

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcatggcag gcaacctgca cctccccgtg                                           30

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttatttgta tgtcgaattt attcgcccaa ctacgtattc cccac                          45

<210> SEQ ID NO 11
<211> LENGTH: 15
<212> TYPE: PRT
<213> ORGANISM: Saccharum sp.

<400> SEQUENCE: 11

Cys Val Glu His Gly Phe Phe Tyr Val Thr Asn His Gly Val Asp
1               5                   10                  15

<210> SEQ ID NO 12
<211> LENGTH: 17
<212> TYPE: PRT
<213> ORGANISM: Saccharum sp.

<400> SEQUENCE: 12

Glu Val Asn Glu Ser Asp Ser Gly Asn Tyr Gly Ala Ser Ala His Ser
1               5                   10                  15

Asp

<210> SEQ ID NO 13
<211> LENGTH: 11
<212> TYPE: PRT
<213> ORGANISM: Saccharum sp.

<400> SEQUENCE: 13

Thr Leu His Arg Val Val Ala Val Gly Lys Glu
1               5                   10

<210> SEQ ID NO 14
<211> LENGTH: 15
<212> TYPE: PRT
<213> ORGANISM: Sorghum bicolor

<400> SEQUENCE: 14

Cys Val Glu His Gly Phe Phe Tyr Val Thr Asn His Gly Val Asp
1               5                   10                  15

<210> SEQ ID NO 15
<211> LENGTH: 17
<212> TYPE: PRT
<213> ORGANISM: Sorghum bicolor -continued

<400> SEQUENCE: 15

Glu Val Asn Glu Ser Asp Ser Gly Asn Tyr Gly Ala Ser Ala His Ser
1               5                   10                  15

Asp

<210> SEQ ID NO 16
<211> LENGTH: 11
<212> TYPE: PRT
<213> ORGANISM: Sorghum bicolor

<400> SEQUENCE: 16

Thr Leu His Arg Val Val Ala Val Gly Lys Glu
1               5                   10

<210> SEQ ID NO 17
<211> LENGTH: 15
<212> TYPE: PRT
<213> ORGANISM: Zea mays

<400> SEQUENCE: 17

Cys Val Glu His Gly Phe Phe Tyr Val Thr Asn His Gly Val Asp
1               5                   10                  15

<210> SEQ ID NO 18
<211> LENGTH: 17
<212> TYPE: PRT
<213> ORGANISM: Zea mays

<400> SEQUENCE: 18

Glu Val His Glu Ser Asp Ser Gly Asn Tyr Gly Ala Ser Ala His Ser
1               5                   10                  15

Asp

<210> SEQ ID NO 19
<211> LENGTH: 11
<212> TYPE: PRT
<213> ORGANISM: Zea mays

<400> SEQUENCE: 19

Thr Leu His Arg Val Val Ala Ile Gly Lys Glu
1               5                   10

<210> SEQ ID NO 20
<211> LENGTH: 15
<212> TYPE: PRT
<213> ORGANISM: Oryza sativa

<400> SEQUENCE: 20

Cys Val Glu Ser Gly Phe Phe Tyr Val Val Asn His Gly Val Glu
1               5                   10                  15

<210> SEQ ID NO 21
<211> LENGTH: 17
<212> TYPE: PRT
<213> ORGANISM: Oryza sativa

<400> SEQUENCE: 21

Glu Val Asp Asp Ser Asp Gly Asn Tyr Gly Ala Ser Ala His Ser
1               5                   10                  15

Asp

<210> SEQ ID NO 22

```
<211> LENGTH: 11
<212> TYPE: PRT
<213> ORGANISM: Oryza sativa

<400> SEQUENCE: 22

Thr Val His Arg Val Val Ala Val Gly Lys Glu
1               5                   10

<210> SEQ ID NO 23
<211> LENGTH: 16
<212> TYPE: PRT
<213> ORGANISM: Oryza sativa

<400> SEQUENCE: 23

Cys Ala Ala His Gly Phe Phe Arg Cys Val Gly His Gly Val Pro Ala
1               5                   10                  15

<210> SEQ ID NO 24
<211> LENGTH: 17
<212> TYPE: PRT
<213> ORGANISM: Oryza sativa

<400> SEQUENCE: 24

Gly Gly Asn Leu Met Ala Gly Gly Arg Ile Gly Phe Gly Glu His Ser
1               5                   10                  15

Asp

<210> SEQ ID NO 25
<211> LENGTH: 11
<212> TYPE: PRT
<213> ORGANISM: Oryza sativa

<400> SEQUENCE: 25

Ile Arg His Arg Val Ile Ala Thr Ala Cys Arg
1               5                   10

<210> SEQ ID NO 26
<211> LENGTH: 15
<212> TYPE: PRT
<213> ORGANISM: Oryza sativa

<400> SEQUENCE: 26

Ala Glu Gln Trp Gly Ala Phe Leu Leu Val Gly His Gly Val Pro
1               5                   10                  15

<210> SEQ ID NO 27
<211> LENGTH: 15
<212> TYPE: PRT
<213> ORGANISM: Oryza sativa

<400> SEQUENCE: 27

Cys Pro Glu Pro Arg Arg Ala Leu Gly Leu Ile Ala His Thr Asp
1               5                   10                  15

<210> SEQ ID NO 28
<211> LENGTH: 11
<212> TYPE: PRT
<213> ORGANISM: Oryza sativa

<400> SEQUENCE: 28

Val Tyr His Arg Ala Val Val Asn Arg Asp Arg
1               5                   10

<210> SEQ ID NO 29
```

```
<211> LENGTH: 15
<212> TYPE: PRT
<213> ORGANISM: Oryza sativa

<400> SEQUENCE: 29

Cys Ala Thr His Gly Phe Phe Gln Val Ser Glu His Gly Val Asp
1               5                   10                  15

<210> SEQ ID NO 30
<211> LENGTH: 15
<212> TYPE: PRT
<213> ORGANISM: Oryza sativa

<400> SEQUENCE: 30

Cys Pro Glu Pro Glu Arg Thr Leu Gly Thr Gly Pro His Cys Asp
1               5                   10                  15

<210> SEQ ID NO 31
<211> LENGTH: 11
<212> TYPE: PRT
<213> ORGANISM: Oryza sativa

<400> SEQUENCE: 31

Cys Leu His Arg Ala Val Val Asn Gln Arg Arg
1               5                   10

<210> SEQ ID NO 32
<211> LENGTH: 15
<212> TYPE: PRT
<213> ORGANISM: Arabidopsis thaliana

<400> SEQUENCE: 32

Cys Glu Glu Phe Gly Phe Phe Lys Val Val Asn His Gly Val Arg
1               5                   10                  15

<210> SEQ ID NO 33
<211> LENGTH: 14
<212> TYPE: PRT
<213> ORGANISM: Arabidopsis thaliana

<400> SEQUENCE: 33

Ala Glu Lys Met Val Lys Val Gly Phe Gly Glu His Thr Asp
1               5                   10

<210> SEQ ID NO 34
<211> LENGTH: 11
<212> TYPE: PRT
<213> ORGANISM: Arabidopsis thaliana

<400> SEQUENCE: 34

Val Lys His Arg Val Leu Ala Asp Thr Arg Arg
1               5                   10

<210> SEQ ID NO 35
<211> LENGTH: 15
<212> TYPE: PRT
<213> ORGANISM: Arabidopsis thaliana

<400> SEQUENCE: 35

Cys Arg Thr Trp Gly Ala Phe Gln Ile Ser Asn His Gly Val Pro
1               5                   10                  15

<210> SEQ ID NO 36
<211> LENGTH: 15
<212> TYPE: PRT
```

```
<213> ORGANISM: Arabidopsis thaliana

<400> SEQUENCE: 36

Cys Pro Glu Pro Asp Arg Ala Met Gly Leu Ala Ala His Thr Asp
1               5                   10                  15

<210> SEQ ID NO 37
<211> LENGTH: 11
<212> TYPE: PRT
<213> ORGANISM: Arabidopsis thaliana

<400> SEQUENCE: 37

Val Leu His Arg Ala Arg Val Asn Gln Thr Arg
1               5                   10

<210> SEQ ID NO 38
<211> LENGTH: 15
<212> TYPE: PRT
<213> ORGANISM: Arabidopsis thaliana

<400> SEQUENCE: 38

Cys Lys Lys His Gly Phe Phe Leu Val Val Asn His Gly Ile Ser
1               5                   10                  15

<210> SEQ ID NO 39
<211> LENGTH: 15
<212> TYPE: PRT
<213> ORGANISM: Arabidopsis thaliana

<400> SEQUENCE: 39

Cys Ile Lys Pro Asp Leu Thr Leu Gly Thr Gly Pro His Cys Asp
1               5                   10                  15

<210> SEQ ID NO 40
<211> LENGTH: 11
<212> TYPE: PRT
<213> ORGANISM: Arabidopsis thaliana

<400> SEQUENCE: 40

Cys Leu His Arg Ala Val Val Asn Ser Glu Ser
1               5                   10

<210> SEQ ID NO 41
<211> LENGTH: 15
<212> TYPE: PRT
<213> ORGANISM: Cucurbita maxima

<400> SEQUENCE: 41

Cys Ser Ser Tyr Gly Phe Phe Gln Ile Val Asn His Gly Ile Pro
1               5                   10                  15

<210> SEQ ID NO 42
<211> LENGTH: 13
<212> TYPE: PRT
<213> ORGANISM: Cucurbita maxima

<400> SEQUENCE: 42

Ala Asp Val Gly Glu Asn Gly Leu Ile His His Glu Asp
1               5                   10

<210> SEQ ID NO 43
<211> LENGTH: 11
<212> TYPE: PRT
<213> ORGANISM: Cucurbita maxima
```

```
<400> SEQUENCE: 43

Ala Thr His Arg Val Val Arg Gln Lys Gly Lys
1               5                   10

<210> SEQ ID NO 44
<211> LENGTH: 15
<212> TYPE: PRT
<213> ORGANISM: Streptomyces jumonjinensis

<400> SEQUENCE: 44

Ala Arg Gly Ser Gly Phe Phe Tyr Ala Ser Asn His Gly Val Asp
1               5                   10                  15

<210> SEQ ID NO 45
<211> LENGTH: 17
<212> TYPE: PRT
<213> ORGANISM: Streptomyces jumonjinensis

<400> SEQUENCE: 45

Val Lys Thr Gly Ala Asp Gly Thr Lys Leu Ser Phe Glu Asp His Leu
1               5                   10                  15

Asp

<210> SEQ ID NO 46
<211> LENGTH: 11
<212> TYPE: PRT
<213> ORGANISM: Streptomyces jumonjinensis

<400> SEQUENCE: 46

Pro Asn His Arg Val Lys Phe Ile Asn Ala Glu
1               5                   10

<210> SEQ ID NO 47
<211> LENGTH: 15
<212> TYPE: PRT
<213> ORGANISM: Zea mays

<400> SEQUENCE: 47

Ala Ala Asp Trp Gly Val Met His Ile Ala Gly His Gly Ile Pro
1               5                   10                  15

<210> SEQ ID NO 48
<211> LENGTH: 15
<212> TYPE: PRT
<213> ORGANISM: Zea mays

<400> SEQUENCE: 48

Cys Pro Gln Pro Glu Leu Ala Val Gly Val Glu Ala His Thr Asp
1               5                   10                  15

<210> SEQ ID NO 49
<211> LENGTH: 11
<212> TYPE: PRT
<213> ORGANISM: Zea mays

<400> SEQUENCE: 49

Val Leu His Arg Gly Leu Val Asn Arg Glu Ala
1               5                   10

<210> SEQ ID NO 50
<211> LENGTH: 15
<212> TYPE: PRT
<213> ORGANISM: Petunia hybrida
```

-continued

```
<400> SEQUENCE: 50

Ala Met Glu Trp Gly Val Met His Leu Val Asn His Gly Ile Ser
1               5                   10                  15

<210> SEQ ID NO 51
<211> LENGTH: 15
<212> TYPE: PRT
<213> ORGANISM: Petunia hybrida

<400> SEQUENCE: 51

Cys Pro Gln Pro Glu Leu Ala Leu Gly Val Glu Ala His Thr Asp
1               5                   10                  15

<210> SEQ ID NO 52
<211> LENGTH: 11
<212> TYPE: PRT
<213> ORGANISM: Petunia hybrida

<400> SEQUENCE: 52

Ile Leu His Arg Gly Val Val Asn Lys Glu Lys
1               5                   10

<210> SEQ ID NO 53
<211> LENGTH: 15
<212> TYPE: PRT
<213> ORGANISM: Petunia hybrida

<400> SEQUENCE: 53

Ser Lys Glu Trp Gly Ile Phe Gln Leu Ile Asn His Gly Ile Pro
1               5                   10                  15

<210> SEQ ID NO 54
<211> LENGTH: 15
<212> TYPE: PRT
<213> ORGANISM: Petunia hybrida

<400> SEQUENCE: 54

Cys Pro Arg Pro Asp Leu Ala Leu Gly Val Val Ala His Thr Asp
1               5                   10                  15

<210> SEQ ID NO 55
<211> LENGTH: 11
<212> TYPE: PRT
<213> ORGANISM: Petunia hybrida

<400> SEQUENCE: 55

Val Tyr His Arg Thr Thr Val Asn Lys Asp Lys
1               5                   10

<210> SEQ ID NO 56
<211> LENGTH: 15
<212> TYPE: PRT
<213> ORGANISM: Hordeum vulgare

<400> SEQUENCE: 56

Cys Glu Asp Trp Gly Ile Phe Gln Val Ile Asp His Gly Val Asp
1               5                   10                  15

<210> SEQ ID NO 57
<211> LENGTH: 15
<212> TYPE: PRT
<213> ORGANISM: Hordeum vulgare

<400> SEQUENCE: 57
```

```
Cys Pro Gln Pro Asp Leu Thr Leu Gly Leu Lys Arg His Thr Asp
1               5                   10                  15
```

<210> SEQ ID NO 58
<211> LENGTH: 11
<212> TYPE: PRT
<213> ORGANISM: Hordeum vulgare

<400> SEQUENCE: 58

```
Ala Asp His Gln Ala Val Val Asn Gly Glu Ser
1               5                   10
```

<210> SEQ ID NO 59
<211> LENGTH: 15
<212> TYPE: PRT
<213> ORGANISM: Arabidopsis thaliana

<400> SEQUENCE: 59

```
Ala Glu Arg Trp Gly Phe Phe Gln Val Val Asn His Gly Ile Ser
1               5                   10                  15
```

<210> SEQ ID NO 60
<211> LENGTH: 15
<212> TYPE: PRT
<213> ORGANISM: Arabidopsis thaliana

<400> SEQUENCE: 60

```
Cys Pro Gln Pro Asp Leu Thr Leu Gly Ile Ser Lys His Thr Asp
1               5                   10                  15
```

<210> SEQ ID NO 61
<211> LENGTH: 11
<212> TYPE: PRT
<213> ORGANISM: Arabidopsis thaliana

<400> SEQUENCE: 61

```
Ala Glu His Arg Val Ile Ala Asn Gly Ser Ser
1               5                   10
```

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 62

```
His His His His His His
1               5
```

<210> SEQ ID NO 63
<211> LENGTH: 322
<212> TYPE: PRT
<213> ORGANISM: Zea mays

<400> SEQUENCE: 63

```
Arg Arg Leu Pro Leu Gln Ala Ser Ala Lys Pro Glu Met Ala Gly Ser
1               5                   10                  15

Leu His Leu Pro Val Val Asp Leu Ala Leu Pro Asp Leu Arg Ala Ala
                20                  25                  30

Ala Glu Ser Ile Arg Gln Ala Cys Val Glu His Gly Phe Phe Tyr Val
            35                  40                  45

Thr Asn His Gly Val Asp Arg Gly Leu Leu Glu Ala Val Phe Ala Glu
```

```
            50                  55                  60
Ser Lys Arg Phe Phe Asp Leu Pro Met Glu Asp Lys Met Ala Leu Leu
 65                  70                  75                  80

Arg Gly Ala Asn His Arg Gly Tyr Thr Pro Pro Tyr Ala Glu Lys Leu
                 85                  90                  95

Asp Ala Ser Ser Gln Phe Val Gly Asp Leu Lys Glu Ser Phe Tyr Ile
            100                 105                 110

Gly Pro Leu Asp Asp Gly Asp Met His Asn Asp Val Asn Gln Trp Pro
        115                 120                 125

Ser Glu Glu Arg Leu Pro Ser Trp Lys Glu Thr Met Lys Leu Tyr Phe
    130                 135                 140

Ala Ala Val Leu Asp Thr Gly Thr Arg Ile Leu Ser Leu Val Ala Leu
145                 150                 155                 160

Gly Leu Asp Leu Asp Ala Asp Phe Phe His Lys Ile Gly Ala Leu Lys
                165                 170                 175

Cys Pro Ser Thr Phe Leu Arg Leu Leu His Tyr Pro Gly Glu Val His
            180                 185                 190

Glu Ser Asp Ser Gly Asn Tyr Gly Ala Ser Ala His Ser Asp Tyr Gly
        195                 200                 205

Met Ile Thr Leu Leu Val Thr Asp Gly Thr Pro Gly Leu Gln Ile Cys
    210                 215                 220

Arg Glu Lys Asp Arg Asn Pro Gln Leu Trp Glu Asp Val His His Ile
225                 230                 235                 240

Asp Gly Ala Leu Ile Ile Asn Ile Gly Asp Leu Leu Glu Arg Trp Thr
                245                 250                 255

Asn Cys Ala Phe Arg Ser Thr Leu His Arg Val Val Ala Ile Gly Lys
            260                 265                 270

Glu Arg Tyr Ser Val Ala Phe Phe Leu Asp Pro Asn Pro Asp Thr Leu
        275                 280                 285

Val Gln Cys Leu Glu Ser Cys Cys Ser Glu Ala Cys Pro Pro Arg Phe
    290                 295                 300

Pro Pro Ile Lys Ser Trp Asp Tyr Ile Ala Gly Arg Leu Asn Ser Thr
305                 310                 315                 320

Tyr Lys

<210> SEQ ID NO 64
<211> LENGTH: 316
<212> TYPE: PRT
<213> ORGANISM: Oryza sativa

<400> SEQUENCE: 64

Met Ala Gly Gly Gly Gly Gly Asn Arg Leu Asp Leu Pro Val Val
  1               5                  10                  15

Asp Leu Ala Ser Ser Asp Pro Arg Ala Ala Glu Ser Ile Arg Lys
                 20                  25                  30

Ala Cys Val Glu Ser Gly Phe Phe Tyr Val Val Asn His Gly Val Glu
             35                  40                  45

Glu Gly Leu Leu Lys Arg Leu Phe Ala Glu Ser Ser Lys Phe Phe Glu
         50                  55                  60

Leu Pro Met Glu Glu Lys Ile Ala Leu Arg Arg Asn Ser Asn His Arg
 65                  70                  75                  80

Gly Tyr Thr Pro Pro Tyr Ala Glu Lys Leu Asp Pro Ser Ser Lys Phe
                 85                  90                  95

Glu Gly Asp Leu Lys Glu Ser Phe Tyr Ile Gly Pro Ile Gly Asp Glu
```

-continued

```
            100                 105                 110
Gly Leu Gln Asn Asp Ala Asn Gln Trp Pro Ser Glu Glu Arg Leu Pro
            115                 120                 125

Ser Arg Arg Glu Thr Ile Lys Met Tyr His Ala Ser Ala Leu Ser Thr
        130                 135                 140

Gly Lys Arg Ile Leu Ser Leu Ile Ala Leu Ser Leu Asn Leu Asp Ala
145                 150                 155                 160

Glu Phe Phe Glu Asn Ile Gly Ala Phe Ser Cys Pro Ser Ala Phe Leu
                165                 170                 175

Arg Leu Leu His Tyr Pro Gly Glu Val Asp Asp Ser Asp Asp Gly Asn
            180                 185                 190

Tyr Gly Ala Ser Ala His Ser Asp Tyr Gly Met Ile Thr Leu Leu Ala
        195                 200                 205

Thr Asp Gly Thr Pro Gly Leu Gln Ile Cys Arg Glu Lys Asn Arg Asn
    210                 215                 220

Pro Gln Leu Trp Glu Asp Val His His Ile Asp Gly Ala Leu Ile Val
225                 230                 235                 240

Asn Ile Gly Asp Leu Leu Glu Arg Trp Thr Asn Cys Ile Tyr Arg Ser
                245                 250                 255

Thr Val His Arg Val Val Ala Val Gly Lys Glu Arg Tyr Ser Ala Ala
            260                 265                 270

Phe Phe Leu Asp Pro Asn Pro Asp Leu Val Val Gln Cys Leu Glu Ser
        275                 280                 285

Cys Cys Ser Glu Ser Cys Pro Pro Arg Phe Ser Pro Ile Lys Ser Gly
    290                 295                 300

Asp Tyr Leu Lys Glu Arg Leu Ser Ala Thr Tyr Lys
305                 310                 315
```